United States Patent [19]
Vlassara et al.

[11] Patent Number: 5,811,075
[45] Date of Patent: Sep. 22, 1998

[54] METHOD AND AGENTS FOR REMOVING ADVANCED GLYCOSYLATION ENDPRODUCTS

[75] Inventors: Helen Vlassara; Michael Brownlee, both of New York; Anthony Cerami, Shelter Island, all of N.Y.

[73] Assignee: The Rockefeller University, New York, N.Y.

[21] Appl. No.: 487,398

[22] Filed: Jun. 7, 1995

Related U.S. Application Data

[63] Continuation of Ser. No. 290,680, Aug. 15, 1994, abandoned, which is a continuation of Ser. No. 162,840, Dec. 3, 1993, abandoned, which is a continuation of Ser. No. 878,837, May 5, 1992, abandoned, which is a continuation of Ser. No. 709,487, Jun. 3, 1991, abandoned, which is a continuation of Ser. No. 453,958, Dec. 20, 1989, abandoned, which is a division of Ser. No. 91,534, Sep. 3, 1987, Pat. No. 4,900,747, which is a continuation-in-part of Ser. No. 907,747, Sep. 12, 1986, abandoned, which is a continuation-in-part of Ser. No. 798,032, Nov. 14, 1985, Pat. No. 4,758,583, which is a continuation-in-part of Ser. No. 590,820, Mar. 19, 1984, Pat. No. 4,665,192.

[51] Int. Cl.[6] .............................. A61K 49/00; C12Q 1/00
[52] U.S. Cl. .................................................. 424/9.1; 435/4
[58] Field of Search ................................... 424/9.1; 435/4

[56] References Cited

U.S. PATENT DOCUMENTS

| | | | |
|---|---|---|---|
| Re. 35,465 | 2/1997 | Vlassara et al. | 514/44 |
| 4,478,744 | 10/1984 | Mezei et al. | 530/322 |
| 4,629,692 | 12/1986 | Dean | 435/7.7 |
| 4,665,192 | 5/1987 | Cerami et al. | 548/315.4 |
| 4,758,583 | 7/1988 | Cerami et al. | 514/399 |
| 4,900,747 | 2/1990 | Vlassara et al. | 514/402 |

FOREIGN PATENT DOCUMENTS

| | | |
|---|---|---|
| 0111211 | 6/1984 | European Pat. Off. . |
| 0259893 | 3/1988 | European Pat. Off. . |
| WO 8504169 | 9/1985 | WIPO . |

OTHER PUBLICATIONS

Vlassara et al. (1987) J. Exp. Med. 166:539–49.
Brownlee et al. (1986) Diabetes 35, Supp. 1:42A.
Brownlee et al. (1986) Science 232:1629–32.
Cerami et al. (1986) J. Cell. Biochem. 30:111–20.
Vlassara et al. (1986) Diabetes 35, Supp. 1:13A.
Kay (1985) Gerontology 31:215–35.
Brownlee et al. (1985) Diabetes 34:938–40.
Vlassara et al. (1985) Diabetes 34:553–7.
Vlassara et al. (1985) Proc. Natl. Acad. Sci. USA 82:5588–92.
Abrass et al. (1984) J. Immuno. 133:1307–12.
Brownlee et al. (1984) Annals Int. Med. 101:527–37.
Handwerger et al. (1984) Imm. Clin. Exp. Diabetes, ed. S. Gupta, N.Y., Plenum, pp. 113–130.
Kohn et al. (1984) Diabetes 33:57–9.
Monier et al. (1984) Proc. Natl. Acad. Sci. USA 81:583–7.
Pongor et al. (1984) Proc. Natl. Acad. Sci. USA 81:2684–8.
Vlassara et al. (1984) J. Exp. Med. 160:197–207.
Brownlee et al. (1983) J. Exp. Med. 158:1739–44.
Dabrowski et al. (1983) Acta Physiol. 34:91–7.
Cornell, (1981) Am. J. Physiol., 240(Gastrointest. Liver Physiol.):G225–31.
Monier et al. (1981) Science 211:491–3.
Silverstein (1981) The Sciences pp. 18–22.
Adams (1979) "Macrophage" Meth. Enzym. Academic Press, NY, vol. LVIII:506.
Rhodes (1975) Nature 257:597–9.
Documenta Geigy (1970) "Scientific Tables", Diom et al eds. Geigy Pharmaceuticals, NY, p. 619 and p. 736.

*Primary Examiner*—Johnny F. Railey, II
*Attorney, Agent, or Firm*—Klauber & Jackson

[57] ABSTRACT

The present invention relates to a method and associated agents for the inhibition and treatment of protein aging in animals by stimulating the bodies of the animals to increase their recognition and affinity for advanced glycosylation end products. Specifically, the method contemplates the administration of certain agents such as advanced glycosylation endproducts, such endproducts as are bound to the carrier, monokines that stimulate phagocytic cells to increase their activity toward advanced glycosylation endproducts, and mixtures of these materials either alone, or in conjunction with other co-stimulatory agents. Numerous diagnostic and therapeutic applications are defined, and pharmaceutical compositions are also contemplated.

13 Claims, 13 Drawing Sheets

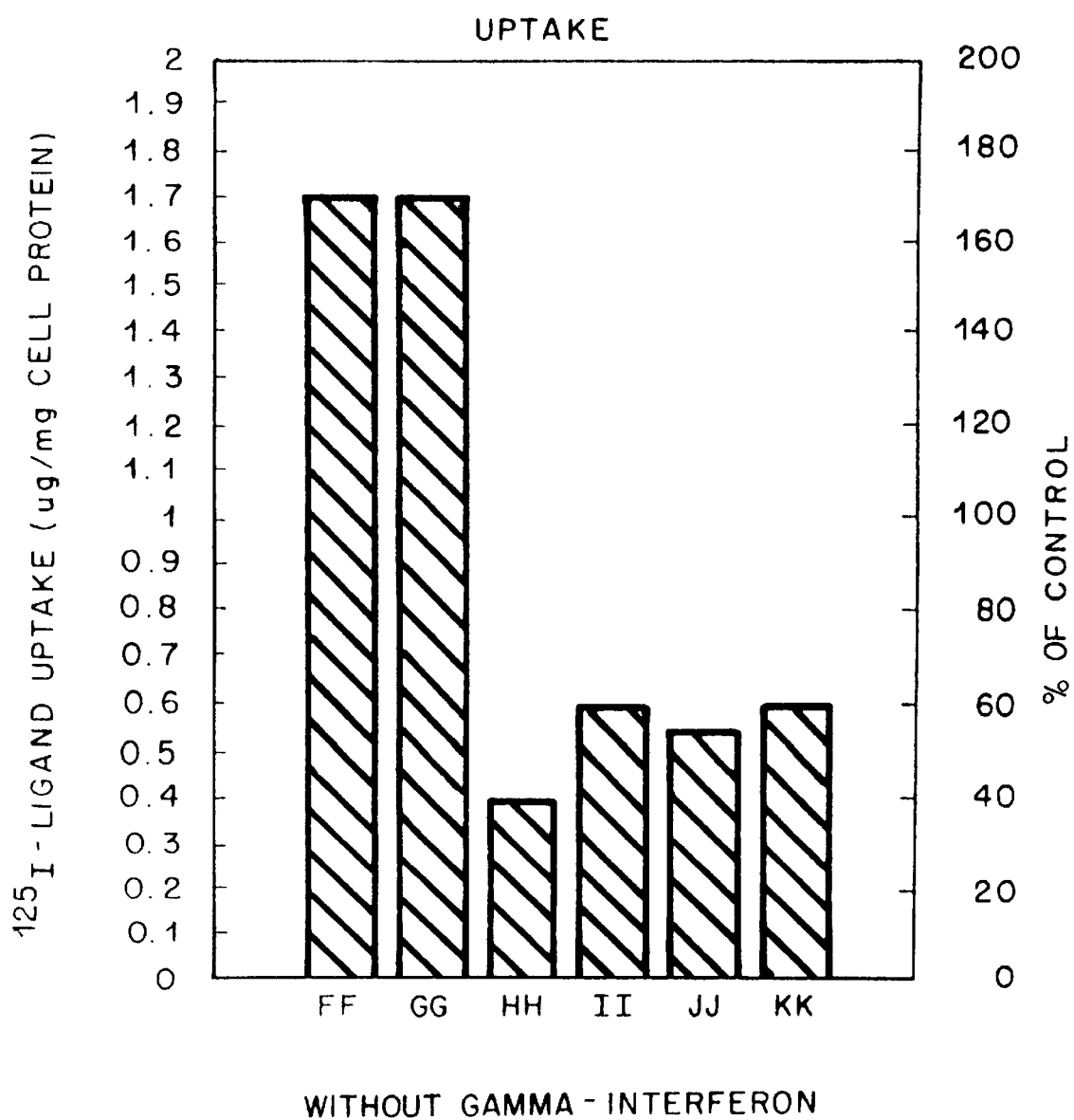

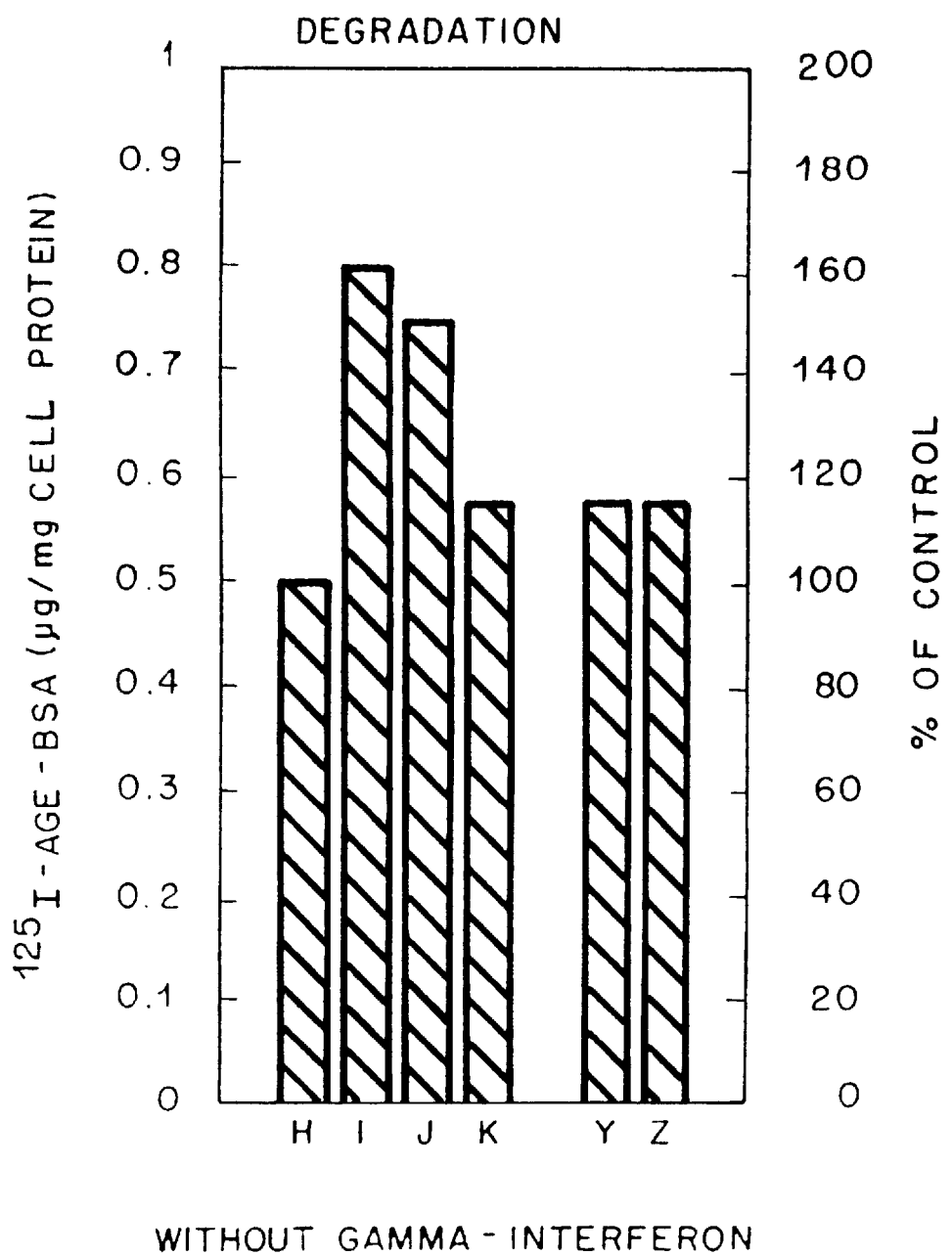

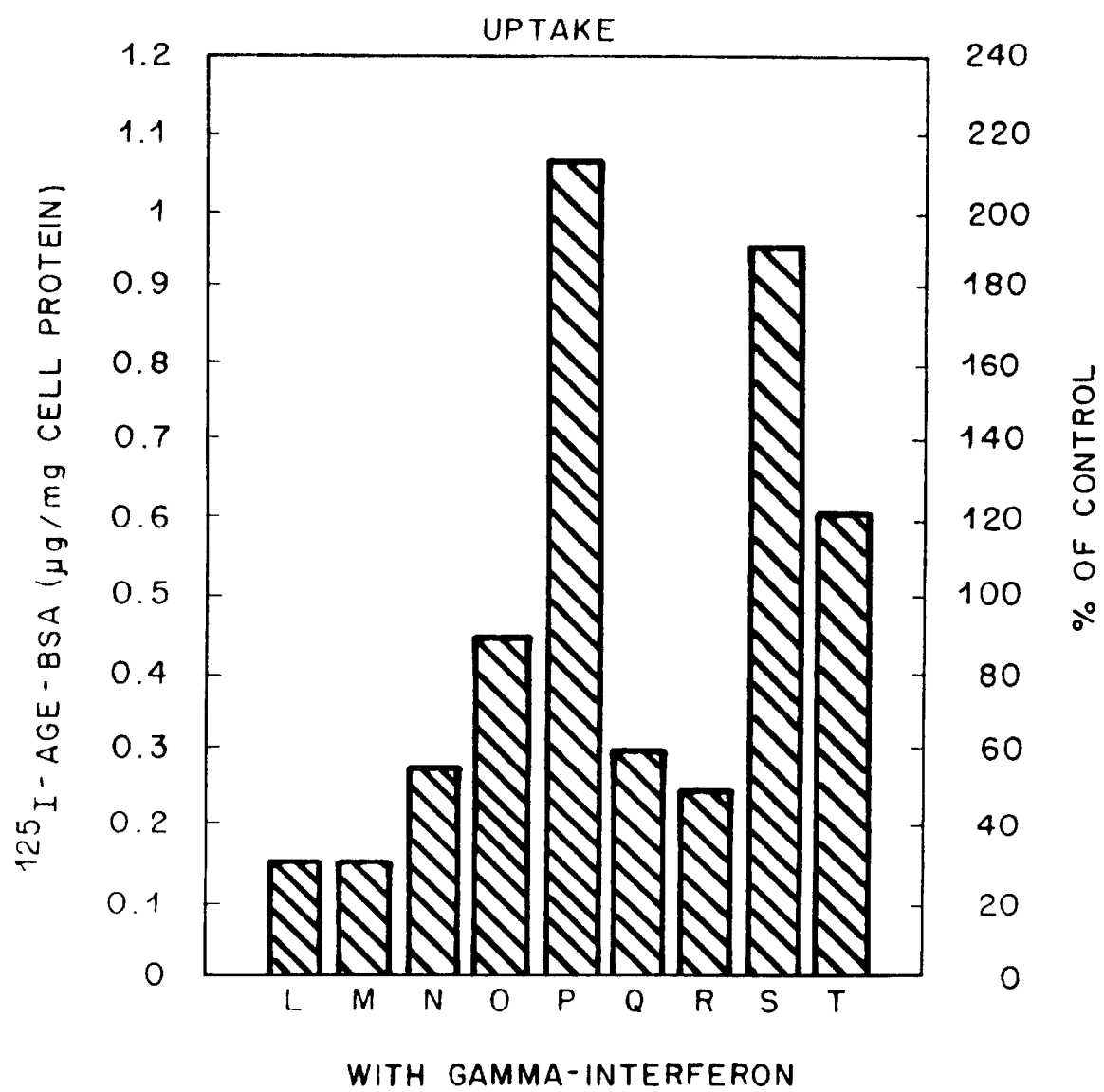

METHOD AND AGENTS FOR REMOVING ADVANCED GLYCOSYLATION ENDPRODUCTS

CROSS REFERENCE TO RELATED APPLICATIONS

The present Application is a Continuation of application Ser. No. 08/290,680, filed Aug. 15, 1994, now abandoned, which is a continuation of Ser. No. 08/162,840, filed Dec. 3, 1993, now abandoned, which is a continuation of Ser. No. 07/878,837, filed May 5, 1992, now abandoned, which is a continuation of Ser. No. 07/709,487, filed Jun. 3, 1991, now abandoned, which is a continuation of Ser. No. 07/453,958, filed Dec. 20, 1989, now abandoned, which is a division al of Ser. No. 07/091,534, filed Sep. 3, 1987, issued as U.S. Pat. No. 4,900,747 and reissued as Re. 35,465, which is a continuation-in-part of Ser. No. 06/907,747, filed Sep. 12, 1986, now abandoned, which is a continuation-in-part of Ser. No. 06/798,032, filed Nov. 14, 1985, now U.S. Pat. No. 4,758,583, which is a continuation-in-part of Ser. No. 06/590,820, filed Mar. 19, 1984, now U.S. Pat. No. 4,665,192.

Priority under 35 U.S.C. §120 is claimed as to all of the above earlier filed applications and the disclosures thereof are incorporated herein by reference.

This invention was made with partial assistance from grants from the National Institutes of Health and the Brookdale Foundation.

RELATED PUBLICATIONS

The Applicants are co-authors of the following articles directed to the subject matter of the present invention: "FUNCTION OF MACROPHAGE RECEPTOR FOR NONENZYMATICALLY GLYCOSYLATED PROTEINS IS MODULATED BY INSULIN LEVELS", Vlassara, Brownlee and Cerami, DIABETES (1986), Vol. 35 Supp. 1, Page 13a; "ACCUMULATION OF DIABETIC RAT PERIPHERAL NERVE MYELIN BY MACROPHAGES INCREASES WITH THE PRESENCE OF ADVANCED GLYCOSYLATION ENDPRODUCTS", Vlassara, H., Brownlee, M., and Cerami, A. J. EXP. MED. ( 1984), Vol. 160, pp. 197–207; "RECOGNITION AND UPTAKE OF HUMAN DIABETIC PERIPHERAL NERVE MYELIN BY MACROPHAGES", Vlassara, H., Brownlee, M., and Cerami, A. DIABETES (1985), Vol. 34, No. 6, pp. 553–557; "HIGH-AFFINITY-RECEPTOR-MEDIATED UPTAKE AND DEGRADATION OF GLUCOSE-MODIFIED PROTEINS: A POTENTIAL MECHANISM FOR THE REMOVAL OF SENESCENT MACROMOLECULES", Vlassara H., Brownlee, M., and Cerami, A., PROC. NATL. ACAD. SCI. U.S.A. (September 1985), Vol. 82, pp. 5588–5592; "NOVEL MACROPHAGE RECEPTOR FOR GLUCOSE-MODIFIED PROTEINS IS DISTINCT FROM PREVIOUSLY DESCRIBED SCAVENGER RECEPTORS", Vlassara, H., Brownlee, M., and Cerami, A. JOUR. EXP. MED. (1986) (in press) "ROLE OF NONENZYMATIC GLYCOSYLATION IN ATHEROGENESIS", Cerami, A., Vlassara, H., and Brownlee, M., Journal of Cellular Biochemistry (1986), Vol. 30, pp. 111–120. All of the foregoing publications are incorporated herein by reference.

BACKGROUND OF THE INVENTION

The present invention relates generally to the in vivo reaction of animal proteins with glucose, and particularly to the nonenzymatic glycosylation of proteins, and to methods for their in vivo inhibition.

The reaction between glucose and proteins has been known for some time, and in its earliest manifestation, was identified in the appearance of brown pigments during the cooking of food. This phenomenon was identified by Maillard in 1912, who observed that glucose and other reducing sugars react with amino acids to form adducts that undergo a series of dehydrations and rearrangements to form stable brown pigments. Maillard L. C. (1912) C.R. Acad. Sci., Vol. 154, pp. 66–68.

This phenomenon was found in recent years to have its parallel in vivo. Accordingly, the nonenzymatic reaction between glucose and the free amino groups on proteins to form a stable amino 1-deoxy ketosyl adduct, known as the Amadori product, has been shown to occur with hemoglobin, wherein a rearrangement of the Amadori product formed at the amino terminal of the beta chain of hemoglobin by reaction with glucose, forms the adduct known as hemoglobin $A_1c$. This initial reaction of the Maillard sequence was also found to occur with a variety of other body proteins, such as lens crystallins, collagen and nerve proteins. See Bunn, H. F., Haney, D. N., Gabbay, K. H. and Gallop, P. H., (1975) Biochem. Biophys. Res. Comm., Vol. 67, pp. 103–109; Koenig, R. J., Blobstein, S. H. and Cerami, A., (1977) J. Biol. Chem., Vol. 252, pp. 2992–2997; Monnier, V. M. and Cerami, A., (1983) MAILLARD REACTION IN FOOD AND NUTRITION, ed. Waller, G. A., American Chemical Society, Vol. 215, pp. 431–448; and Monnier, V. M. and Cerami, A., (1982) Clinics in Endocrinology and Metabolism, Vol. 11, pp. 431–452.

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 and 90 years. See Monnier, V. M. and Cerami, A., (1981) SCIENCE, Vol. 211, pp. 491–493; Monnier, V. M. and Cerami, A., (1983) BIOCHEM. BIOPHYS. ACTA., Vol. 760, pp. 97–103; and Monnier, V. M., Kohn, R. R. and Cerami, A., "Accelerated Age-related Browning of Human Collagen in Diabetes Mellitus", (1984) PROC. NAT. ACAD. SCI., Vol. 81, pp. 583–587. Interestingly, the aging of collagen can be mimicked in vitro by the cross-linking induced by glucose; and the capture of other proteins in the formation of adducts by collagen, also noted, is theorized to occur by a cross-linking reaction, and is believed to account for the observed accumulation of albumin and antibodies in kidney basement membrane and cholesterol-bearing low density lipoprotein in the arterial wall. See, Brownlee, M., Pongor, S. and Cerami, A., (1983) J. EXP. MED., Vol. 158, pp. 1739–1744; and Konn, R. R., Cerami, A. and Monnier, V. M., (1984) DIABETES, Vol. 33, No. 1, pp. 57–59. Cerami, A., Vlassara, H., and Brownlee, M., (1985) METABOLISM, Vol. 34, pp. 37–44.

In parent application Ser. No. 590,820 and in Pongor, S. M. et al, Supra., both incorporated herein by reference, a fluorescent chromophore was isolated and identified which was found to be present in certain browned polypeptides such as bovine serum albumin and poly-L-lysine, and was assigned a structure 2-(2-furoyl)-4(5)-2-furanyl)-1H-imidazole (hereinafter "FFI"). The compound was found to exist in a tautomeric state and has incorporated in its structure two peptide-derived amine nitrogens. The incorporation of these amine nitrogens and two glucose residues in the compound suggested that its peptide-bound precursor may be implicated in the in vivo cross-linking of proteins by glucose which is observed in the late stage of the Maillard process. See, Chang, J. C. F., Ulrich, P. D., Bucala, R., and Cerami, A., (1985) J. Biol. Chem., Vol 260, pp. 7970–7974. This chromophore made possible the identification of the advanced glycosylation endproducts and assisted additional investigations seeking to clarify the protein aging process and if possible, to identify the specific chemistry involved to assist efforts to develop methods and agents for its inhibition. Such method and agents were initially investigated and have been disclosed in copending application Ser. No. 798,032, the disclosure of which is incorporated herein by reference.

Further work since the development of the inhibitors in the last mentioned copending Application resulted in the identification of what appears to be an endogenous means for the in vivo elimination or removal of advanced glycosylation endproducts. This has been set forth in most recent application Ser. No. 907,747. Further development of this concept is now presented herein, and it is accordingly to this purpose that the present Application is directed.

SUMMARY OF THE INVENTION

In accordance with the present invention, a method and associated agents are disclosed for the inhibition and treatment of protein aging in animals by stimulating the bodies of such animals to increase their recognition of and affinity for advanced glycosylation endproducts. In particular, phagocytic cells such as monocytes and macrophages are treated with an agent capable of causing the phagocytic cells to increase their activity of recognizing and removing macromolecules such as target proteins.

The agents of the present invention comprise one or more stimulator compounds in turn, comprising a natural or synthetic advanced glycosylation endproduct alone or bound to a carrier, said carrier including a material selected from carbohydrates, proteins, synthetic polypeptides, lipids, biocompatible natural and synthetic resins, antigens, and mixtures thereof. The stimulator compounds could include other advanced glycosylation endproducts that may be prepared from the reaction between sugars and other macromolecules, and monokines which stimulate phagocytic cells to increase their activity toward advanced glycosylation endproducts.

Accordingly, the stimulator compound may comprise the compound FFI bound to a protein such as albumin. Alternately, the stimulator compound Ray comprise a synthetically derived advanced glycosylation endproduct which is prepared, for example, by the reaction of glucose or glucose-6-phosphate with albumin. This reaction product can be used alone or with a carrier in the same fashion as the FFI-albumin complex.

A monokine that functions as a stimulator compound comprises the protein known as Tumor Necrosis Factor (TNF) and its variant discovered and isolated by one of the inventors herein and named "cachectin". This material may be administered alone or in conjunction with other stimulator compounds.

In addition, the stimulator compounds of the present invention may be administered in conjunction with materials identified hereinafter as "co-stimulatory agents". The coadministration of the stimulator compound with the co-stimulatory agents has been found to potentiate the activity of the former. Suitable co-stimulatory agents include monokines such as Interleukin-1 (IL-1) and gamma-interferon.

A further alternative embodiment of the method of the present invention and one which may be practiced independently or conjointly with the above recited method, is the ex vivo treatment of the phagocytic cells to expose them to the stimulator compounds. For example, a patient may be given an extracorporeal blood treatment in which blood is diverted out of the body from the arterial and venous system and is directed through a device which contains stimulator compounds and/or co-stimulatory agents which are suitably positioned to come in contact with the phagocytic cells within the blood. The stimulator compounds and/or co-stimulatory agents may be immobilized or may be allowed to enter the flow of the body fluid.

In the instance where the method comprises the in vivo administration of the stimulator compound and/or stimulatory agents, such administration may be accomplished by known techniques, including oral techniques and parenteral techniques such as intradermal, subcutaneous, intravenous, or intraperitoneal injection, catheterization or other conventional means. The stimulator compounds or mixtures of them may be prepared in suitable pharmaceutical compositions for such administration.

In a further aspect of the present invention, phagocytic cells may be stimulated to increase their ability to recognize and remove target macromolecules by adjustment of the insulin level in the body fluid. In particular, artificial reduction of insulin levels may be achieved by dietary manipulation and/or by the use of pancreatic beta-cell suppression, conducted alone or in combination with the administration of the agents discussed above. Thus, this additional method exerts a positive effect on the activity of the phagocytic cells and promotes the increased uptake and elimination of advanced glycosylation endproducts in accordance with the present invention.

In addition, the present invention relates to various therapeutic methods, for the treatment of the adverse sequelae of the build-up of advanced glycosylation endproducts in the body. In particular, pathologies such as age related or diabetes related hardening of the arteries, skin wrinkling, arterial blockage and diabetic retinal and renal damage are all the result of the excessive build-up or trapping that occurs as the presence of advanced glycosylation endproducts increases. Accordingly, a therapeutic method in accordance with the present invention generally seeking to avert such pathologies contemplates the administration of the agents of the present invention either directly or in suitable pharmaceutical compositions to stimulate the phagocytic cells to remove advanced glycosylation endproducts from the body with greater speed and efficiency, and to thereby avert the onset of the pathologies recited herein. Specific administrative protocols may vary and would be determined upon the specific instruction of qualified medical or veterinary practitioners.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as a result of prolonged exposure to blood sugar and AGE formation. Consequently, the enhanced ability to remove glycosylation endproducts from the animal's system carries the promise of favorably treating the significant adverse effects of numerous pathologies including diabetes and of course, improving the quality and perhaps duration of animal life.

A further therapeutic application of the present invention lies in the area of immunology. In particular, advanced glycosylation endproducts generally, and FFI in particular, may be coupled to antigens, and phagocytic cells may then be exposed to this coupled complex to promote the uptake and digestion of this coupled complex by such cells. The phagocytic cells would then present the digested complex to the immune system of the animal of origin to elicit the development of antibodies to the particular antigen. In this manner, antigens that might not otherwise elicit an immunologically significant response could be made more immunologically reactive to develop effective defenses to the antigen. The foregoing method could be practiced in vivo or ex vivo, as, for example, the coupled complex including the advanced glycosylation endproduct or FFI could either be introduced into the body of the animal, or phagocytic cells could be isolated from the animal in extracorporeal fashion and thereby contacted with the coupled complex, after which the phagocytic cells with their increased receptors could be reintroduced into the animal's body to appropriately stimulate the immune system to develop antibodies.

A variant to the foregoing protocol contemplates the stimulation of the phagocytic cells to take direct action against the antigen. In this procedure, an antibody specific to the target antigen is labeled with or coupled to an advanced glycosylation endproduct such as FFI, and the labeled/coupled material is then introduced in vivo to promote the arousal of the activity of the phagocytes toward this material. The labeled/coupled material would bind to the target antigen and the resulting complex would be attacked by the phagocytes that recognize the AGE or FFI. Attack would occur either directly or by the secretion of a monokine such as cachectin to cause the necrosis of the antigen. The phagocytes could be preliminarily activated by in vivo or ex vivo means as described earlier. This protocol, like the one described above, possesses particular utility as a possible treatment for Acquired Immune Deficiency Syndrome (AIDS) and other tumorous or viral infections.

In addition, the present invention contemplates certain diagnostic applications, including the development of an assay system for screening of potential drugs effective to act as agents to stimulate the activity of particular phagocytic cells against advanced glycosylation endproducts. In one instance, a prospective test drug could be administered to a macrophage sample to determine its stimulatory effect, with control samples receiving, respectively, a known stimulator compound such as those listed above, and no stimulation whatsoever. Further, a particular phagocytic cell sample could be investigated to determine the agents from among those known that are most effective in stimulating such cellular activity, if such stimulation is possible, by the inoculation of a series of identical sample colonies with various of the known agents recited above, with such agents being appropriately labeled by a radioactive indicator or otherwise, to chart the activity or progress in stimulation, by the uptake of such agents by the particular cellular colony. In such manner, the colony exhibiting the greatest uptake and disposal of labeled advanced glycosylation endproducts would identify the corresponding agent that is most effective in this stimulatory capacity.

By the above diagnostic techniques, cellular colonies capable of stimulation could be determined, and in the instance where such capability is in evidence, the colonies could be further examined to determine whether any discrimination in the particular agent capable of achieving such stimulation is in evidence.

Additional diagnostic applications relate to the study of a variety of parameters attending the recognition and removal of advanced glycosylation endproducts by phagocytic cells and the significance of this phenomenon in relation to the functioning of the animal's system. In a first embodiment, phagocytic cells such as macrophages may be removed from the animal's body and activated ex vivo by exposure to advanced glycosylation endproducts. These activated phagocytic cells may then be radiolabeled as with Technicium and thereafter reintroduced to the animal and allowed to circulate through the animal's system, while being radioimaged to note the final location of the cells. In this manner, the location of concentrations of advanced glycosylation endproducts in the animal's body could be identified. This technique is particularly useful in identifying undesireable concentrations of advanced glycosylation endproducts, such as atheromatous plaques. In such manner, the location of the systemic malfunction could be identified.

Also, the condition of the system for the removal of advanced glycosylation endproducts from the body could be measured by the preparation of radiolabeled advanced glycosylation endproducts and the administration of these radiolabeled materials to the body to determine the time required for their recognition, uptake and elimination. Such measurement could then be compared against standard measurements determined by testing normal systems under the same parameters. The foregoing test could, for example, be performed as a test for diabetes, or other disorders that would adversely effect the operability of the AGE removal system of the body. Alternately, this method may likewise be practiced in extracorporeal fashion by removing phagocytic cells from the body and testing them for their efficiency and rate of operation ex-vivo with radiolabeled advanced glycosylation endproducts.

A further diagnostic technique could measure the presence of pathology as a function of the state of activation of the phagocytic cells in the body of the animal under investigation. Thus, macrophage cells could be exposed to particular radiolabeled advanced glycosylation endproducts known to be found in connection with certain pathologies, and the state of stimulation of the phagocytic cells could then be observed, by comparison against suitably developed norms, to determine whether the phagocytic cells are in a state of stimulation, and if so, as to the probable source of such stimulation. Thus, the presence of particular AGEs in the body reflect correspondingly particular pathologies, and the observation of the phagocytic cells and the determination of their sensitivity and increased stimulation with respect to particular advanced glycosylation endproducts would suggest the existence of a particular pathology.

Accordingly, it is a principal object of the present invention to provide a method for improved sequestration and removal of advanced glycosylation endproducts from animal systems.

It is a further object of the present invention to provide a method as aforesaid which is characterized by the stimulation of phagocytic cells to increase their affinity and capability for the binding, uptake and degradation of advanced glycosylation endproducts.

It is a yet further object of the present invention to provide agents capable of stimulating phagocytic cells to bind, take up and degrade advanced endproducts in the method as aforesaid.

It is a still further object of the present invention to provide therapeutic methods for treating the adverse consequences of protein aging.

Other objects and advantages will become apparent to those skilled in the art from a consideration of the ensuing description which proceeds with reference to the following illustrative drawings.

BRIEF DESCRIPTION OF THE DRAWINGS

FIG. 5A is a bar graph illustrating the comparative uptake of advanced glycosylation endproducts by mouse microphages exposed to the following stimulator compounds: FF, cachectin (20 mg)+Glu-BSA; GG, cachectin (20 mg)+G6P-BSA; HH, control Glu-BSA; II, control G6P-BSA; JJ, IL-1+G6P-BSA; and KK, LPS+G6P-BSA. Experiments FF, GG, JJ, and KK each included 25 µg of the respective AGE reagent.

FIG. 6B is a bar graph illustrating data similar to that set forth in FIG. 5B with respect to one day old human monocytes. The various additions are as follows: H, control; I, cachectin; J, IL-1; K, gamma-interferon; Y, all FFI-BSA; and Z, all G6P-BSA. Each experiment with AGE contained 25 µg of the respective AGE-BSA.

FIG. 7A is a bar graph illustrating similar comparative experiments as that in FIG. 6A conducted with human monocytes wherein the costimulatory agent gamma-interferon was also added and tested. The various stimulator compounds included: L, control; M, gamma-interferon only; N, FFI-BSA (0.1 mg/ml); O, FFI-BSA (0.02 mg/ml); P, FFI-BSA (0.05 mg/ml); Q, FFI-BSA (0.1 mg/ml); R, G6P-BSA (0.25 mg/ml); S, G6P-BSA (0.5 mg/ml); and T, G6P-BSA (0.5 mg/ml).

DETAILED DESCRIPTION OF THE PREFERRED EMBODIMENT

Figure 1:
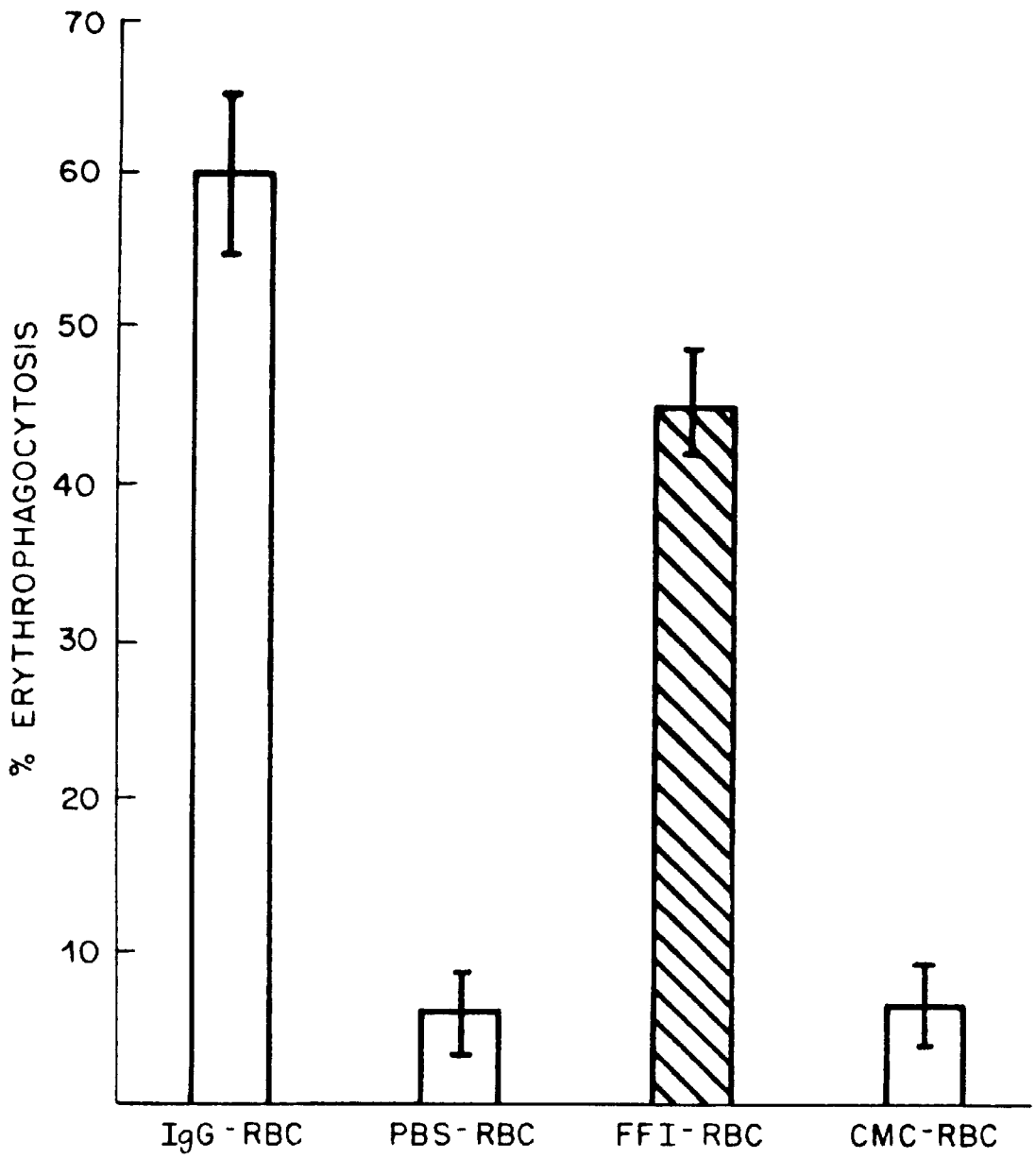
FIG. 1 is a graph depicting the relative binding and uptake of red blood cells modified with various agents, including one of the agents of the present invention.

In accordance with the present invention, a compostion and associated methods have been developed for enhancing the removal of advanced glycosylation endproducts in animals, to treat protein aging and thereby inhibit the adverse effects thereof. Specifically, phagocytic cells such as monocytes and macrophage cells are exposed to one or more agents or stimulator compounds which enhance the ability of such phagocytic cells to recognize, bind and degrade advanced glycosylation endproducts.

The present invention is predicated upon the observation that monocytes and macrophage cells have the ability to recognize, remove and degrade macromolecules that have undergone glucose-mediated damage and thus have undergone advanced glycosylation endproduct formation. In particular, it has been determined that monocytes and macrophages have a specific surface receptor for the glucose-altered macromolecules that allows the cells to perform their recognition, removal and degrading functions with respect thereto.

Previous work with respect to glucose-mediated changes in proteins has determined that glucose reacts with such macromolecules and leads to changes in their properties which interfere with their normal function. Glucose is known to react specifically with the amino groups of proteins without the aid of enzymes to cause them to become crosslinked or to covalently bind to and thereby trap other proteins.

In particular, glucose may initially react with an amino group on a protein and thereby form what is known as a reversible Schiff base adduct. The abduct then rearranges to form a more stable, but still reversible Amadori product. The Amadori product, which is an initially glycosylated protein may then undergo further reactions, which in one instance, include the reaction with a second glycosylated amino group of a protein, whereby a crosslink is formed. The result of this reaction is the conversion of the two glucose moieties and their amino groups into a compound identified previously by one of the inventors herein and referred to earlier as FFI. This compound is part of a complex family of advanced glycosylation endproducts that exhibit yellow and fluorescent appearance. The presence of this compound has been confirmed by the in vitro reaction of glucose and proteins, whereby the resulting mass is observed to become yellow to brown in color. These advanced glycosylation endproducts form simply from the reaction of sugars with proteins and other macromolecules, including DNA.

The Amadori product can also react with a second glucose, and the resulting doubly glycosylated derivative can then react directly with the amino group of a non-glycosylated protein to form an advanced glycosylation endproduct (AGE) and to thereby link the proteins together. This phenomenon has been termed "trapping" and has been demonstrated in vitro by the reaction of collagen, a normally insoluble, structural protein, and low-density lipoprotein, which is a circulating, soluble protein, as well as collagen with albumin and IgG. See Brownlee, M., et al., DIABETES, Vol. 34, pp. 938–941 (1985); Brownlee, M., Pongor, S., and Cerami A., J. EXP. MED., Vol. 158, pp. 1739–1744 (1983).

Glucose mediated crosslinking and trapping of proteins is a normal process in the body which over time leads to pathology in many tissues and organs. Internal crosslinking of proteins or crosslinking of two adjacent proteins may change the mechanical properties of structural proteins. Changes in the immunologic, enzymatic, physical and other properties as a result of crosslinking and trapping are also known. For example, it has been observed that the abnormally high level of glucose in the blood of diabetics leads to an abnormal increase in the formation of crosslinks and trapped proteins, and it is postulated that this may be responsible for the increased morbidity and mortality of the disease.

Trapping leads to an abnormal build up of proteins in abnormal locations which can lead to pathology. Examples of the pathology that can be caused by glucose-mediated crosslinking and trapping includes the attachment of lipoprotein and other plasma proteins to the walls of coronary arteries, and its consequent build up of proteins and cholesterol to cause arterial blockage and heart attacks. Similarly, crosslinking of collagen in the arterial wall can change the mechanical properties of the arterial wall by stiffening its structure and thereby causing circulatory problems. Thickening of basement membranes of smaller blood vessels in the body and in the kidney resulting from trapping and crosslinking leads to peripheral vascular disease and thickening of the kidney basement membrane with subsequent loss of kidney function (Nephropathy). In addition, thickening of vessel walls in the brain leads to reduced blood flow and can contribute to the onset of senility.

Crosslinking of collagen and other macromolecules in the skin may lead to wrinkling and other changes, as well as changes in the diabetic eye and particularly damage to the lens and to the vessels of the retina, which latter event leads to a loss of visual acuity and ultimately, to blindness. Finally, glucose is known to react with DNA, and experiments have shown that AGE-DNA can be mutagenic in bacteria.

As noted earlier, phagocytic cells are capable of recognizing and removing abnormal macromolecules by means of receptors on their surfaces which recognize specific chemical structures and bind to them. Once the abnormal macromolecule is recognized in this way, the phagocytic cell may internalize the macromolecule or particle containing the abnormal macromolecule and may then degrade it. In some instances, the phagocytic cell may in addition secrete enzymes and other factors to help degrade the molecule or particle extracellularly if it cannot be internalized. After the damaged protein is removed, new growth of normal tissue can ensue, and normal function of the affected area may resume.

Phagocytic cells in the body comprise numerous types of white blood cells. One type of white blood cell, the monocyte, is produced in the bone marrow, and circulates briefly in the blood and thereafter enters the tissues where it becomes a macrophage. Exposure of the phagocytic cell either as a monocyte or a macrophage, to certain molecules can regulate the appearance on the surface of the cell of receptors for these molecules.

Thus, the present invention is predicated on the discovery that the phagocytic cells including monocytes and macrophages can be modified by exposure to certain agents or stimulator compounds that potentiate the capability of these cells with respect to their recognition and affinity for, and capability to degrade advanced glycosylation endproducts. In particular, the exposure of these cells to certain stimulator compounds has been found to increase the number of receptors developed on these cells and to thereby increase the capacity and efficiency of these cells with respect to the recognition and degradation of advanced glycosylation endproducts.

Accordingly the method of the present invention generally comprises exposing the animal body to certain agents or stimulator compounds, which cause the body, and its phagocytic cells in particular to become activated and to increase its recognition and removal of target macromolecules that have undergone advanced glycosylation.

Suitable stimulator compounds useful in the present invention comprise materials including advanced glycosylation endproducts either naturally or synthetically formed which may be employed alone or bound to a carrier.

Suitable stimulator compounds include the compound FFI bound to a carrier protein such as the protein albumin. The stimulator compound may also comprise a synthetically derived advanced glycosylation endproduct which is prepared, for example, by the reaction of a protein or other macromolecule with a sugar such as glucose, glucose-6-phosphate, or others. This reaction product could be used alone or could be combined with a carrier in the same fashion as the FFI-albumin complex.

The carrier may be selected from the group consisting of carbohydrates, proteins, synthetic polypeptides, lipids, biocompatible natural and synthetic resins, antigens and mixtures thereof.

As used herein, the term "antigen" includes various invasive stimuli that may comprise or cause the onset of pathology or other organic disability, such as protein and lipid fragments, bacteria, viruses and/or other organisms of similar origin and effect.

Stimulator compounds also include other monokines which stimulate phagocytic cells to increase their activities toward advanced glycosylation endproducts.

A particular monokine that functions as a stimulator compound comprises the protein known as Tumor Necrosis Factor (TNF) and its variant discovered and isolated by one of the inventors herein and named "cachectin". This material may be administered alone or in conjunction with other stimulator compounds.

In addition, the stimulator compounds of the present invention may be administered in conjunction with materials identified hereinafter as "co-stimulatory agents". The coadministration of the stimulator compound with the co-stimulatory agents has been found to potentiate the activity of the former. Suitable co-stimulatory agents include monokines such as Interleukin-1 (IL-1) and gamma-interferon.

With regard to the preparation of the stimulator compound comprising FFI coupled to a carrier molecule such as albumin, the synthetic compound FFI-hexanoic acid may be used in its preparation. Thus, a water-soluble carbodiimide is used to attach the acid moiety of the FFI-hexanoic acid to an amino group on the protein. This conjugate, after purification, is used in vitro to stimulate macrophages. After incubation for 4 to 24 hours, it can be shown that such macrophages will more actively bind, internalize, and degrade AGE-albumin.

Accordingly, the present invention includes various therapeutic methods seeking to treat the adverse effects of the buildup of advanced glycosylation endproducts in animals. Such conditions as age- or diabetes- related hardening of the arteries, skin wrinkling, arterial blockage and diabetic retinal and renal damage all result from the excessive buildup or trapping that occurs as advanced glycosylation endproducts increase in quantity. Accordingly, a therapeutic method seeking to avert pathologies caused at least in part by the accumulation of advanced glycosylation endproducts in the body comprises the administration of the agents of the present invention either directly or in suitable pharmaceutical compositions to stimulate the body the increase its activity toward the recognition and removal of such advanced glycosylation endproducts. In particular, the agents are administered to stimulate the phagocytic cells in the body to increase their activity toward the recognition and removal of advanced glycosylation endproducts so that such removal occurs with greater speed and efficiency. Specific administrative protocols would vary and would be determined upon the instruction of qualified medical or veterinary practitioners.

Accordingly, the present invention also includes suitable pharmaceutical compositions for use in the therapeutic methods of the invention, comprising the agents of the present invention prepared in a suitable pharmaceutically acceptable carrier. Such carriers are known and may vary in composition and/or concentration depending upon the manner of administration, i.e. oral, parenteral, etc.

The present invention will be better understood from a consideration of the following illustrative examples and data, that confirm the activities of the phagocytic cells and their relationship to the stimulator compounds discovered in accordance herewith.

EXAMPLE I

In the investigation which follows, the existence in vivo of the clearance system of advanced glycosylation endproducts was confirmed and studied, and the principles of the present invention were established.

MATERIALS AND METHODS

RBC preparation: Human Blood (2.0 ml) from normal, healthy adult volunteers was collected in heparinized tubes. Following removal of plasma and buffy coat, the RBC's were washed four times with 10 vol of $Ca^{2+}$ and $Mg^{2+}$ free phosphate-buffered saline (PBS), pH 7.4 and were resuspended in Dulbecco's modified Eagle medium.

Opsonized RBC preparation: 0.1 ml of a 15% RBC suspension from a $D^+$ donor was added to 0.5 ml of a high-titer anti-D serum and was incubated at 37° C. for 30 minutes. Following incubation, cells were washed three times with PBS (GIBCO) and were resuspended in 3 ml of Dulbecco's modified Eagle medium.

FFI-RBC preparation: The specific advanced glycosylation endproduct (AGE) [2-(2-furoyl)-4(5)-(2-furanyl)-1H-imidazole]-hexanoic acid (FFI-HA) was prepared as described previously (Pongor et al., PNAS (1984) Vol. 81, pp. 2684–2688). In brief, furylglyoxal hydrate (10 mmol) in 3:1 dioxane/water was treated with 6-amino hexanoic acid (15 mmol) and triethylamine (15 mmol) and stirred at 25° C. for 1 hour. After the addition of concentrated aqueous ammonia, the mixture was diluted with 5% $NaH_2PO_4$ and extracted with $CH_2Cl_2$, washed with brine and filtered through activated carbon and $MgSO_4$. The crude product was purified by medium pressure chromatography on silica gel yielding FFI-HA as straw-colored flakes (m.p. 105°–106° C.). Freshly washed normal RBC's were resuspended in PBS, with and without 10 mM water soluble 1-cyclohexyl-3-[2-(4-morpholinyl)-ethyl]-carbodiimide (CMC) (Vlassara, et al., (1985), Vol. 82, pp. 5588–5592), to which FFI-HA was added at different concentrations (10–100 μM). The mixtures were incubated under continuous mixing for 1 hour at room temperature. Parallel mixtures containing RBC's alone in PBS or RBC's and carbodiimide (10 mM) were treated identically as controls. After 3 washes the cells were resuspended in 1 mM glycine in PBS and left to incubate for 30 minutes. Following three washings with PBS the cells were suspended in RPMI prior to phagocytosis assay, at an 100 excess ratio to monocytes.

Glycosylated-RBC preparation: In order to produce nonenzymatically glycosylated erythrocytes, glucose, glucose-6-phosphate, xylose and arabinose were added to freshly isolated normal human red cells suspended in Dulbecco's modified Eagle medium at 100 mM concentrations and incubated for 48 hours at room temperature. RBC suspensions without sugars added were used as control cells. Following the incubation, the cells were washed three times with PBS and were suspended in RPMI.

AGE-BSA was prepared by incubating bovine serum albumin (BSA) in 50 mM glucose at 37° C. for 6 weeks, in the presence of protease inhibitors (PMSF 1.5 mM, EDTA 0.5 mM) and antibiotics (penicillin 100 U/ml, gentamicin 40 mg/ml) See, Vlassara et al., Supra.)

Human monocyte preparation: The buffy coat from 100 ml fresh human blood was diluted two-fold with saline 1 mM EDTA, pH 7.4, and mononuclear cells were separated from other elements of the blood by centrifugation on Ficoll-Paque gradients as described before (Gimelig-Meyling et al. (1950), J. IMMUN. METHODS, Vol. 33, p. 1). The mononuclear cells were washed three times in cold RPMI 1640 (GIBCO) to remove platelets, and the cells were suspended in RPMI made 10% in normal human serum. To obtain suspensions of monocytes for use in these experiments, the Percoll purification method described previously was used (Gimelig-Meyling supra.). Percoll was brought to isotonicity by the addition of 0.1 vol. of 10-x concentrated PBS. One ml of normal human serum, 14.7 ml PBS, and 22 ml isotonic Percoll was mixed in sterile 50-ml centrifuge tubes and centrifuged for 25 minutes at 18,000 rpm at 5° C. in a Sorvall SS-34 rotor. Five ml of the mononuclear suspension were layered on the resulting gradients and the tubes were centrifuged at 1,500 g for 25 minutes at 5° C. in a swinging bucket rotor. The resulting bands were detected by light scattering and band I, corresponding to monocytes was transferred and cultured in screw cap Teflon jars (Savillex, Minnetonka, Minn.), at $10^6$/ml in RPMI with 12.5% human serum at 37° C. in 5% $CO_2$ for 5–7 days. Cell viability was assessed by trypan blue exclusion (Gibco Lab.) and plating efficiency of phagocytes on a tissue-culture plastic surface was measured by a hemocytometer before and after attachment. When ready for use, aliquots of $10^6$ monocytes were plated in sterile petri dishes containing precleaned round coverslips and incubated for 2 hours at 37° C. in 5% $CO_2$.

Phagocytosis assay: Before the addition of RBC's the monocyte cultures were washed twice with RPMI 1640. The various red cell suspensions were added to each well at a 100 fold excess to the monocytes and were allowed to incubate at 37° C. and 5% $CO_2$ for up to 2 hours. At that point the coverslips were removed from the wells, washed three times with RPMI to remove nonadherent material, placed into clean wells and fixed with 1.25% glutaraldehyde in PBS for 30 minutes. To differentiate surface-attached from ingested erythrocytes, a hypotonic solution (PBS diluted 1:4 in $H_2O$)

was added to selected wells for 10 seconds, followed by the addition of fixative. To read the assay, duplicate coverslips were counted using 40× phase microscopy. At least 300 monocytes from three or more randomly selected fields were counted per well. The data were expressed as the number of positive monocytes (monocytes with erythrocytes attached or ingested) per 100 monocytes (percent binding). Ingestion index was also determined as the number of ingested or adhered red cells per positive monocyte (Bianco et al. (1976) J. EXP. MED., Vol. 144, p. 1531).

FFI-RBC ½ life assay: Balb/c inbred mice were bled by cardiac puncture yielding approximately 2.0 ml of blood. Red cells were washed with large volumes of divalent cation-free PBS and coupled with FFI-HA as described above in the presence of 10 mM CMC. In addition, RBC's incubated in CMC alone or PBS alone were used as controls. Subsequently all cell suspensions were labeled with $^{51}$Cr by adding 0.2 mCi $Na_2[^{51}Cr]O_4$ to 2 ml of 50% packed RBC in RPMI-1640 medium for 1 hour at 37° C. The labeled cells were washed at least four times to remove unbound isotope. Twelve Balb/c mice were then injected intravenously with 200 μl RBC suspension. Each sample was administered in three Balb/c mice. At appropriate time intervals the mice were bled (0.2 ml) and radioactivity levels were measured by counting.

RESULTS

Maximum binding of red cells was observed on Day-7 of monocyte incubation in vitro. Maximum binding and endocytosis of FFI-RBC was complete within 30–45 minutes while opsonized cells were maximally bound within 15 minutes. At the end of one hour incubation of FFI-coupled RBC's with cultured human monocytes, per cent phagocytosis and phagocytic index were estimated. As shown in FIG. 1, % erythrophagocytosis of FFI-modified red cells (55%) and IgG-coated red cells (70%) were significantly higher than that of control PBS-treated cells (4%). Similarly the phagocytic index of FFI-treated RBC's was significantly elevated (3.4) as compared to normal controls (1.2).

Figure 2:
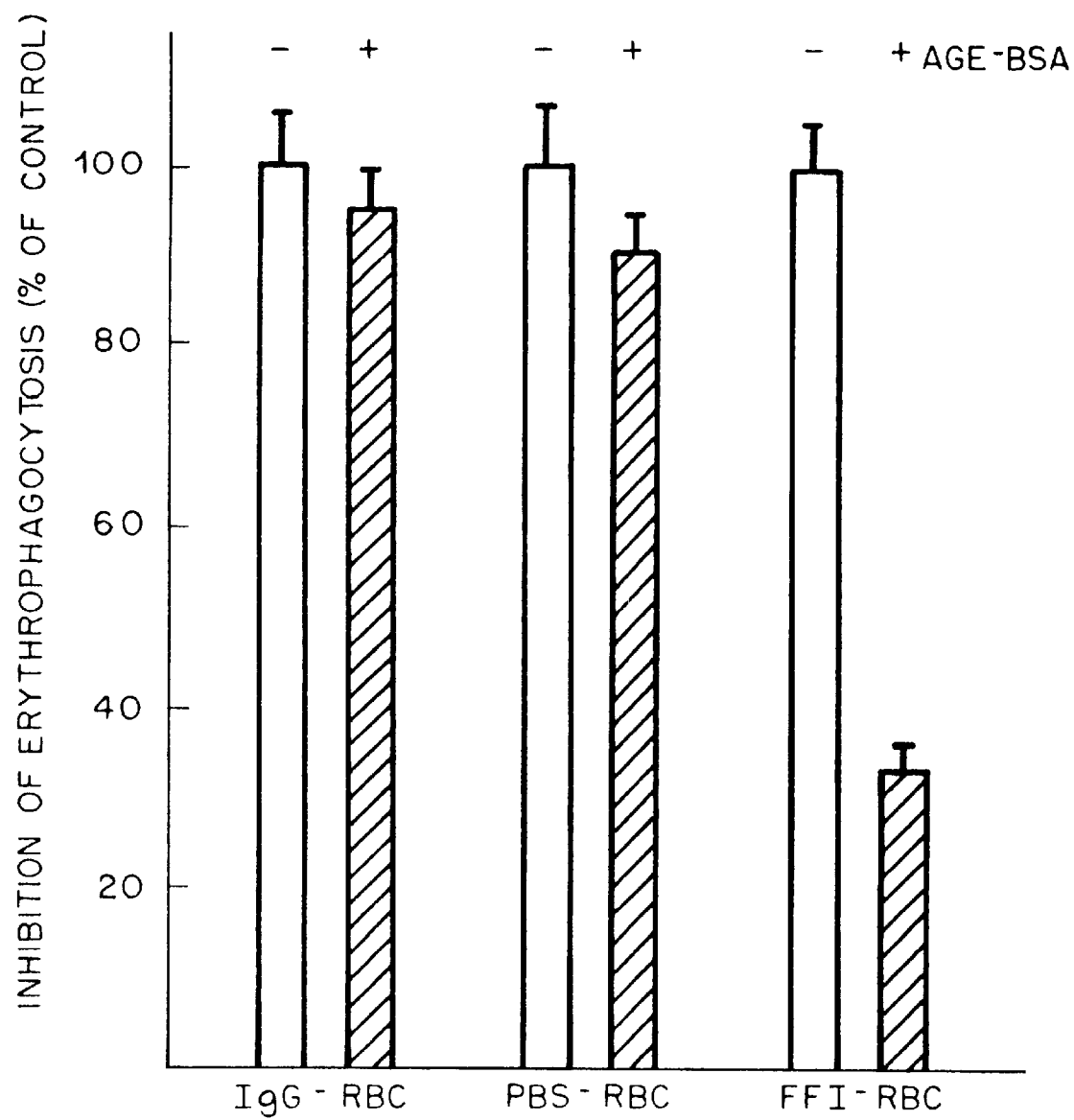
FIG. 2 is a graph illustrating the competitive inhibition in red blood cell binding caused by the introduction into a sample of an agent in accordance with the present invention.

In order to establish the specificity of the interaction of FFI-RBC's with the human monocytes, competition experiments were carried out in which binding and ingestion of red cells was observed in the absence and presence of AGE-BSA, prepared as described in Methods (Vlassara et al., supra.). As shown in FIG. 2, the addition of AGE-BSA at concentrations of 500 μg/ml inhibited the FFI-RBC binding by more than 70% of the control. In contrast, AGE-BSA did not inhibit opsonized or PBS-treated red cells, even at maximal concentrations (1 mg/ml). These data suggested that FFI-modified red cells were recognized and bound specifically by the monocyte AGE-binding site.

Figure 3:
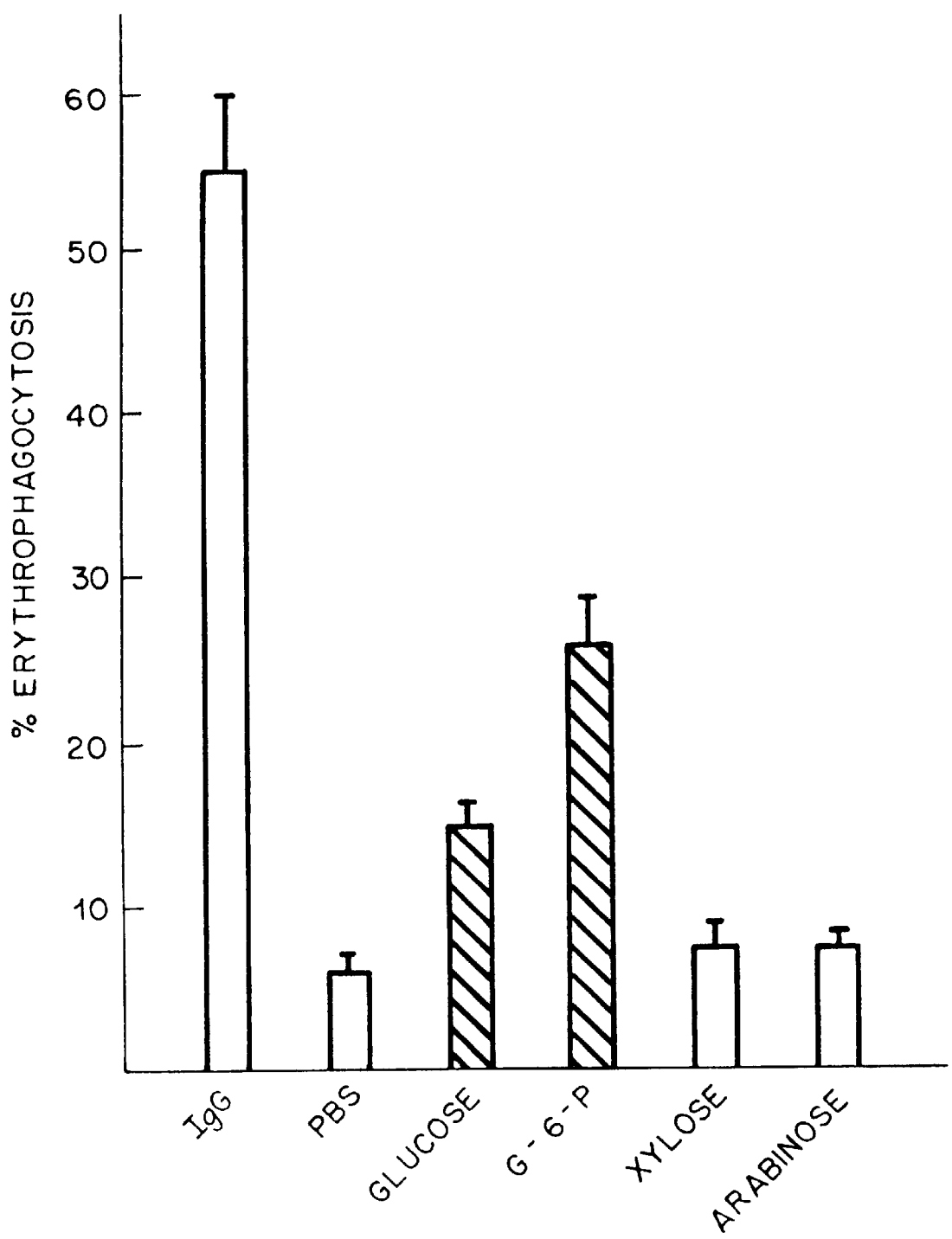
FIG. 3 illustrates the binding and uptake by monocytes of red blood cells that have been modified by reaction with a variety of sugars.

Advanced glycosylation endproduct (AGE) formation was then induced on red cell surfaces by 48 hour incubation in Dulbecco's modified Eagle medium containing different sugars, such as glucose, glucose-6-phosphate, xylose and arabinose, at 100 mM concentrations, at room temperature. At the end of this period, the media demonstrated no evidence of cell lysis, and red cells themselves appeared microscopically indistinguishable from the controls. As demonstrated by RIA (the method of Chang et al., (1985) J. BIOL. CHEM., Vol. 260, pp. 7970–7974), all cells incubated in sugar underwent formation of a significant amount of advanced glycosylation endproducts on their cell membrane, as compared to the controls. At this point RBC's from all groups were subjected to normal human monocyte phagocytosis assay. As indicated in FIG. 3, glucose-incubated RBC's showed a 15% binding and ingestion and G6P-treated RBC's at 26%, as compared to 6% binding and ingestion of control PBS-RBC's. Much lower level of binding were noted with red cells preincubated with xylose and arabinose (7.5% each).

Figure 4:
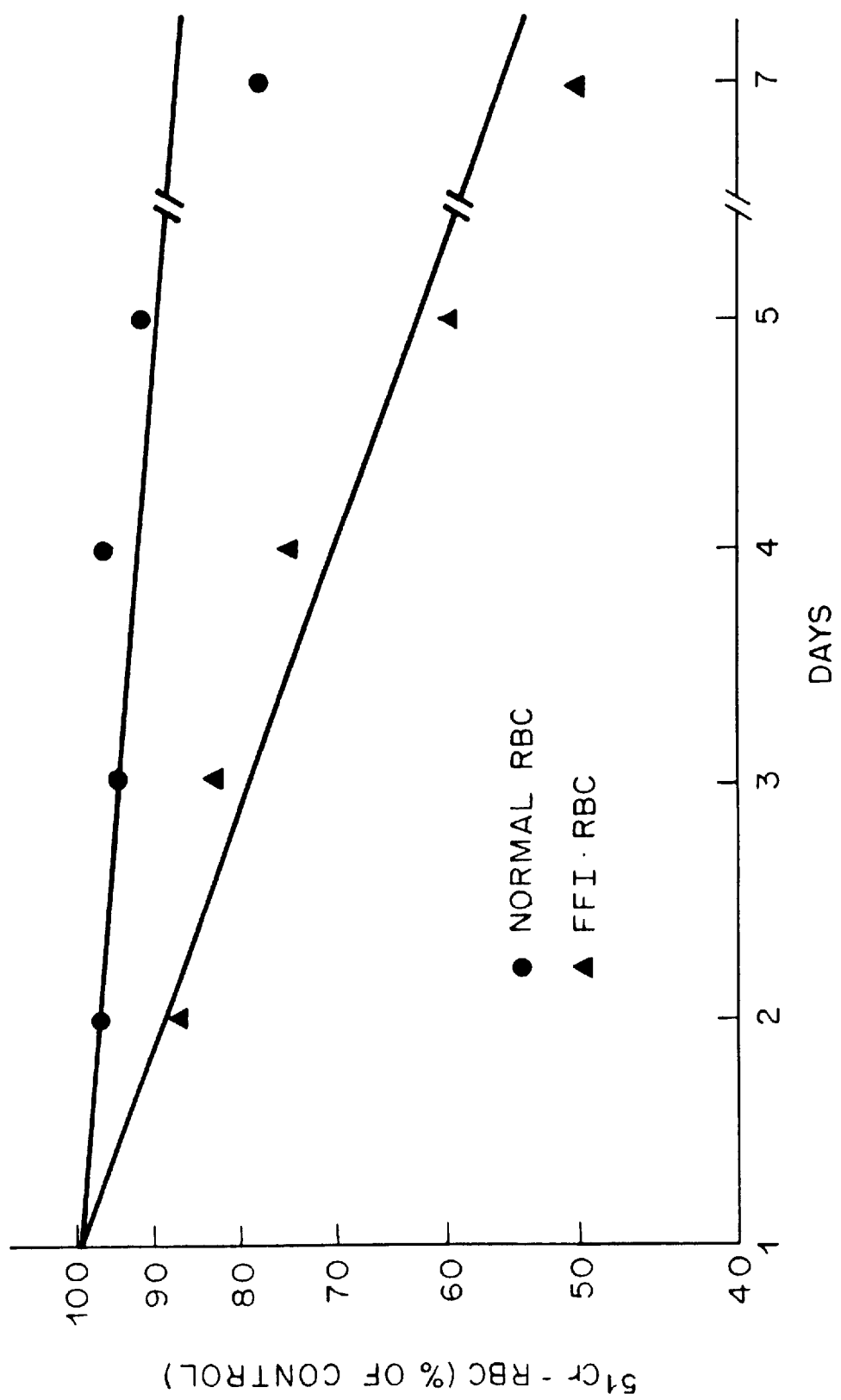
FIG. 4 is a line graph illustrating the half-life of red blood cells that have been labeled and modified by association with an agent in accordance with the present invention, as compared with a control.

In order to determine whether autologous red blood cells modified by an AGE such as FFI-HA can be recognized by macrophages in vivo and be removed from the circulation faster than the non-modified cells, presumably by the same AGE-receptor present on hepatic and splenic macrophages, Balb/c inbred mouse red cells were treated either with FFI-HA, as described in Methods, or PBS alone for one hour at room temperature. As an additional control, mouse cells were treated with carbodiimide alone (10 mM). Following $^{51}$Chromium-labeling all three groups of cells were reinjected intravenously into syngenetic mice and erythrocyte radioactivity was monitored for 20 days. An approximate 9% of initial radioactivity recovered from all groups within the 1 hour of the injection was recovered in the serum fraction, presumably due to traumatic hemolysis caused by the ex vivo handling since it was reduced to 0.4% within the first 24 hours. As shown in FIG. 4, the half-life of FFI-treated red cells was reduced to 7 days, as compared to the control untreated cell half-life of approximately 20 days. Similarly, cells treated with carbodiimide alone had nearly normal in vivo course.

DISCUSSION

The above tests extend previous observations on the recognition of advanced glycosylation endproducts (AGE) by a specific monocyte/macrophage receptor, and present evidence that such adducts once attached chemically or formed in vitro on the surface of intact human cells can induce cell binding and ingestion by normal human monocytes. It is demonstrated that the presence of AGE on the cell surface in significant amounts over the unmodified cells leads to their shortened survival in vivo, presumably due to the more rapid removal of these AGE-cells by the splenic and hepatic phagocytic cells. The mechanism of recognition and removal of such modified cells appears to be mediated via the specific macrophage AGE-receptor, as shown by the competitive inhibition only of AGE-red cell binding in the presence of large excess of AGE-BSA (Vlassara et al., supra.).

With age, nonenzymatically glycosylated proteins normally undergo further modifications and rearrangements leading to the formation of increasing amounts of AGE's, as was shown in normal human dura collagen (Monnier et al. (1984) PNAS, Vol. 81, pp. 583–587). One specific endproduct, FFI, has been identified in vivo on normal human serum albumin and globin (Pongor et al., (1984) PNAS, Vol. 81, p. 2684). The AGE-receptor recognition increases with the amount of AGE, and can therefore preferentially recognize a time-dependent signal for the removal of senescent macro-molecules (Vlassara et al. supra.).

Nonenzymatic glycosylation of erythrocyte membrane proteins has been shown previously (Miller et al., (1980) J. CLIN INVEST. Vol. 65, pp. 896–901) to occur primarily at the lysine residues of all the major protein bands without distinction and is enhanced in diabetes, while it is decreased in hemolytic anemia. These findings have suggested that the modification of membrane proteins, other than by blood glucose, depends not only on glucose concentration, but also on erythrocyte age. The foregoing experiments demonstrate that AGE is present on normal intact red blood cells, which may be responsible in part for daily removal of erythrocytes from the circulation by the monocyte/macrophage AGE-receptor. Further, AGE accumulation can be accelerated by exposure to high glucose levels, which in turn leads to increased monocyte AGE-receptor binding and ingestion of glucose-modified red cells, and this may play a role in the moderately shortened erythrocyte survival in diabetics (Peterson, C. M., et al., (1977) ANN. INT. MED., Vol. 86, pp. 425–429).

The difference in erythrocyte binding between glucose and glucose-6-phosphate-treated cells is probably due to the higher amount of AGE formed, owing to the presence of a higher percentage of more reactive open ring structures in the incubation mixture in the case of glucose-6-phosphate. Suprisingly, even though xylose and L-arabinose both can react faster with protein amino groups than glucose, as shown by the amount of AGE formed, they did not induce binding and uptake above the normal control cells. This phenomenon warrants further investigation, however it is probably due to formation of glycosylation products which are not recognized by the AGE or any other monocyte receptor.

EXAMPLE II

The following series of experiments were performed to measure the ability of agents to stimulate phagocytic cells to stimulate uptake and degradation of endproducts (AGEs).

Accordingly, a number of AGEs were prepared using the same procedure as disclosed in Example I, above. Thus, FFI-HA was prepared as described and quantities were bound to both human and bovine albumin. A water soluble carbodiimide was used to attach the acid moiety of the FFI-HA to an amino group on the protein. After preparation, the conjugate was purified and then used in vitro to stimulate macrophages, by incubation for from 4 to 24 hours. The AGEs that were to be observed for uptake and degradation were appropriately radiolabeled so that they could be traced. Thereafter, the stimulated macrophages were tested by exposure to the radiolabeled AGEs following exposure to various agents to measure the effect that these agents had on the ability of the macrophages to take up and degrade the labeled AGEs. The above procedures and the studies that follow conform to the protocol employed by Vlassara et al., supra.

Figure 6A:
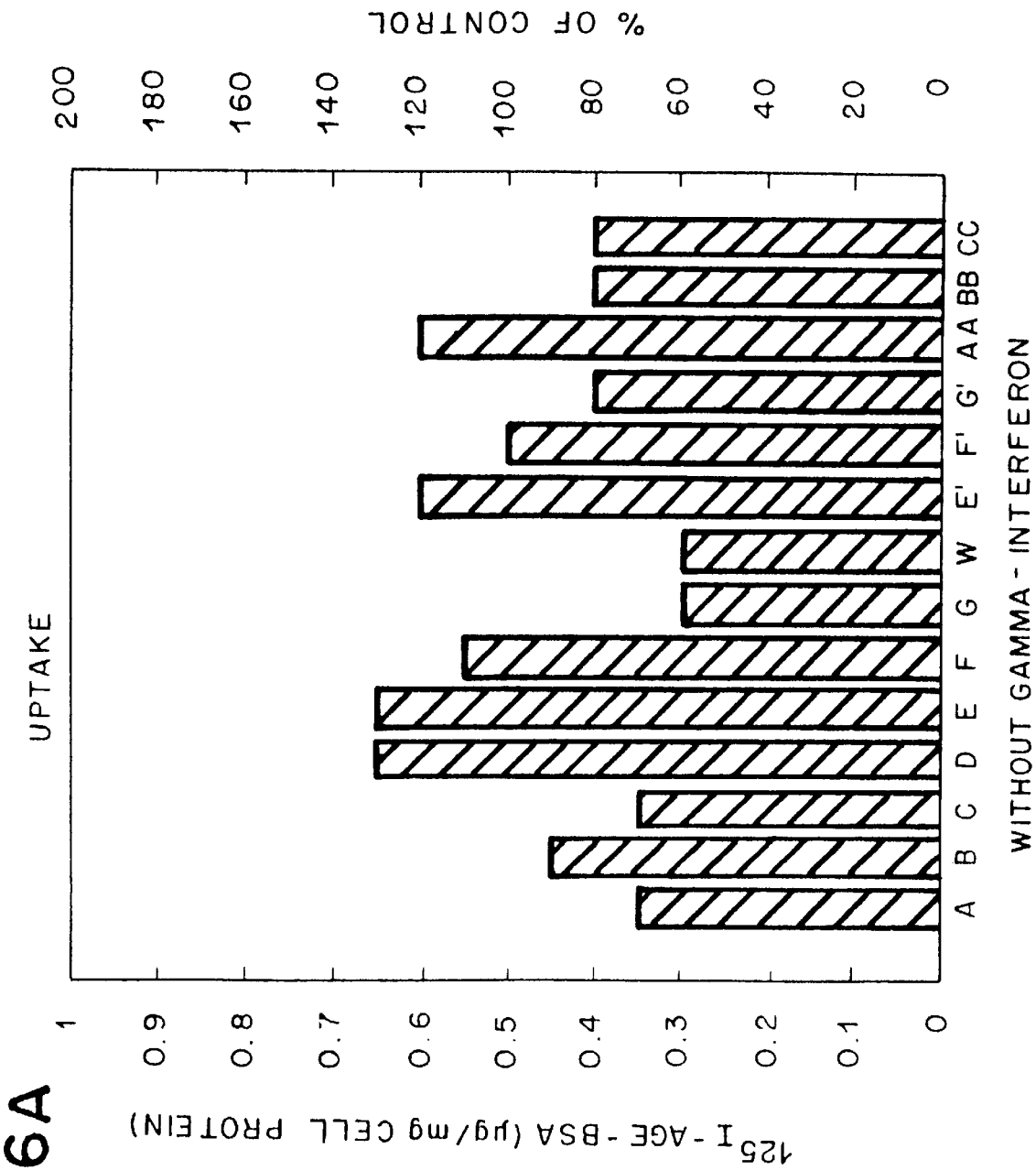
FIG. 6A is a bar graph illustrating data similar to that set forth in FIG. 5A with respect to one day old human monocytes. The key to the experiments and the various stimulator compounds is as follows: A, control; B, LPS; C, gamma-interferon; D, cachectin; E, human FFI-ALB (0.1 mg/ml); F, human FFI-ALB (0.2 mg/ml); G, human FFI-ALB (0.5 mg/ml); W, IL-1; E', FFI-BSA (0.05 mg/ml); F', FFI-BSA (0.01 mg/ml); G', FFI-BSA (0.1 mg/ml); AA, G6P-BSA (0.1 mg/ml); BB, G6P-BSA (0.5 mg/ml); and CC, G6P-BSA (1.0 mg/ml).

Thus, FIG. 6A shows the uptake of AGF-BSA by human monocytes after stimulation with certain agents in the absence of gamma-interferon. The FFI-human albumin at 0.1 and 0.2 mg/ml had a stimulatory effect on the uptake system (bars E and F, respectively) as compared to the control (bar A). FFI-bovine albumin is also stimulatory (bars E', F', and G'). Gamma-interferon alone (bar C), or lipopolysaccharide alone (bar B) or Interleukin-1 alone (bar W) have no stimulatory effect.

Figure 7B:
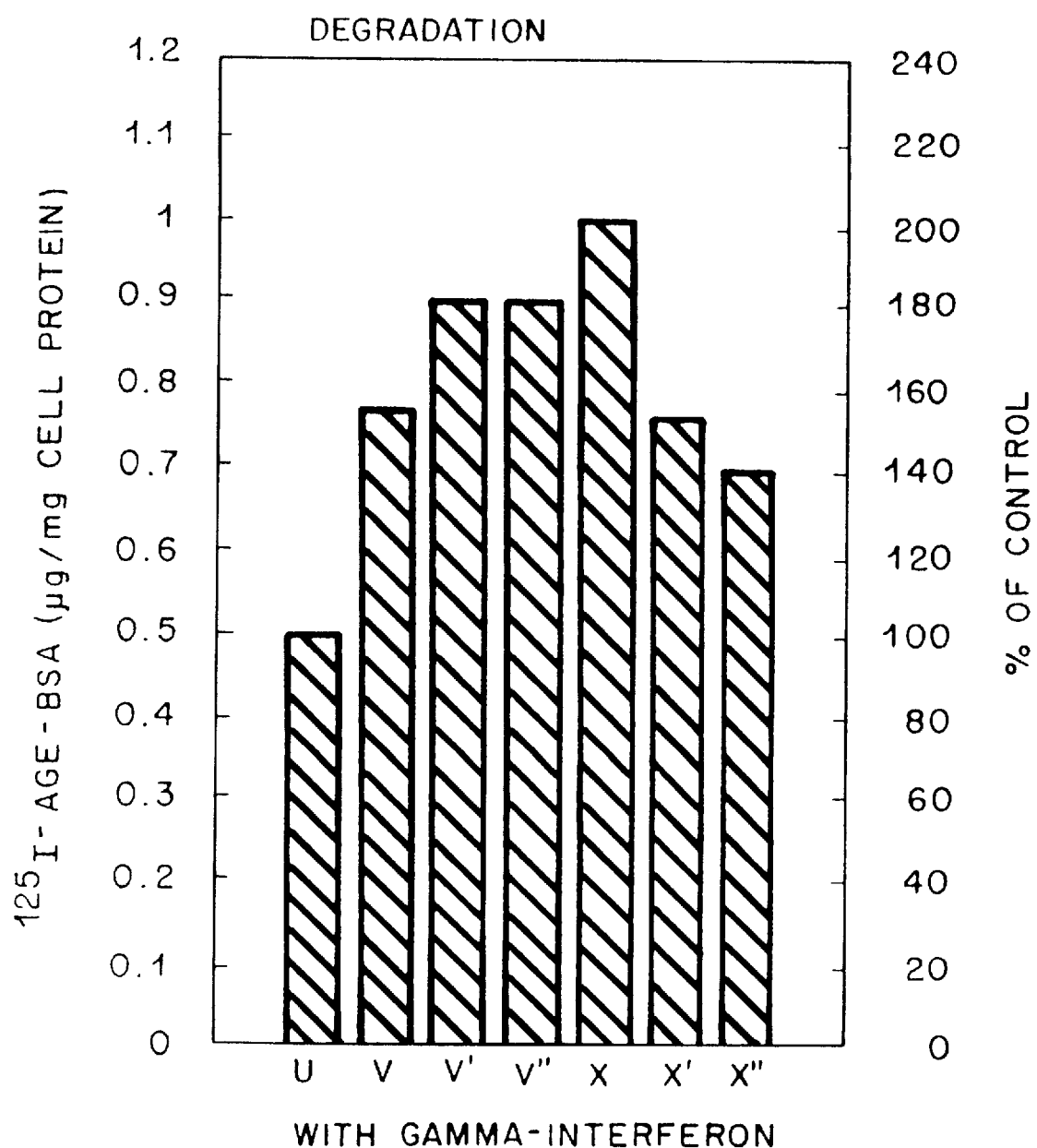
FIG. 7B is a bar graph illustrating similar comparative experiments as that in FIG. 6B conducted with human monocytes wherein the costimulatory agent gamma-interferon is also added and tested. The various stimulator compounds were: U, control; V, FFI-BSA (0.01 mg/ml); V', FFI-BSA (0.05 mg/ml); V", FFI-BSA (0.1 mg/ml); X, G6P-BSA (0.1 mg/ml); X', G6P-BSA (0.25 mg/ml); and X", G6P-BSA (0.5 mg/ml).

FIG. 6B shows the degradation of AGE-BSA by human monocytes in the presence of these agents, in the absence of gamma-interferon. The FFI-BSA preparations are slightly stimulatory (bar Y). In FIG. 7A, the effect of stimulation on the uptake of AGE-BSA by the same agents in the presence of 10 micrograms/ml of human gamma-interferon is shown. As can be seen, gamma-interferon greatly potentiates (up to 8-fold) the stimulation by 0.01, 0.02, and 0.05 mg/ml of FFI-BSA (bars N, O and P). Degradation is also enhanced in the presence of these agents plus gamma-interferon (FIG. 7B, bar V).

It has also been demonstrated that monocyte or macrophage cells can also be stimulated by AGE-carrier molecules which result in cells with enhanced ability to bind, internalize and degrade other AGE-molecules. AGE-carrier molecules are made, for example, from the reaction of glucose or glucose-6-phosphate with albumin. After purification of the reaction product, the AGE-albumin uptake of AGE-macromolecules demonstrated as in (A) above. AGE-BSA (prepared from the incubation of glucose-6-phosphate with albumin for 6–8 weeks) at 0.1 mg/ml has a stimulatory effect on AGE-BSA uptake by human monocytes (FIG. 6A, bar AA), and shows a slight stimulation at higher concentrations (bars BB and CC). FIG. 7A, bar S, shows that in the presence of gamma-interferon, 0.5 mg/ml of AGE-BSA made from glucose-6-phosphate, greatly stimulates uptake of AGE-BSA by macrophages. The lower concentrations show a slight stimulatory effect (bars Q and R).

Degradation of AGE-BSA by human monocytes is also stimulated by AGE-BSA in the presence of gamma-interferon (FIG. 7B, bar X). Without interferon, stimulation is slight (FIG. 6B, bar Z).

Figure 5B:
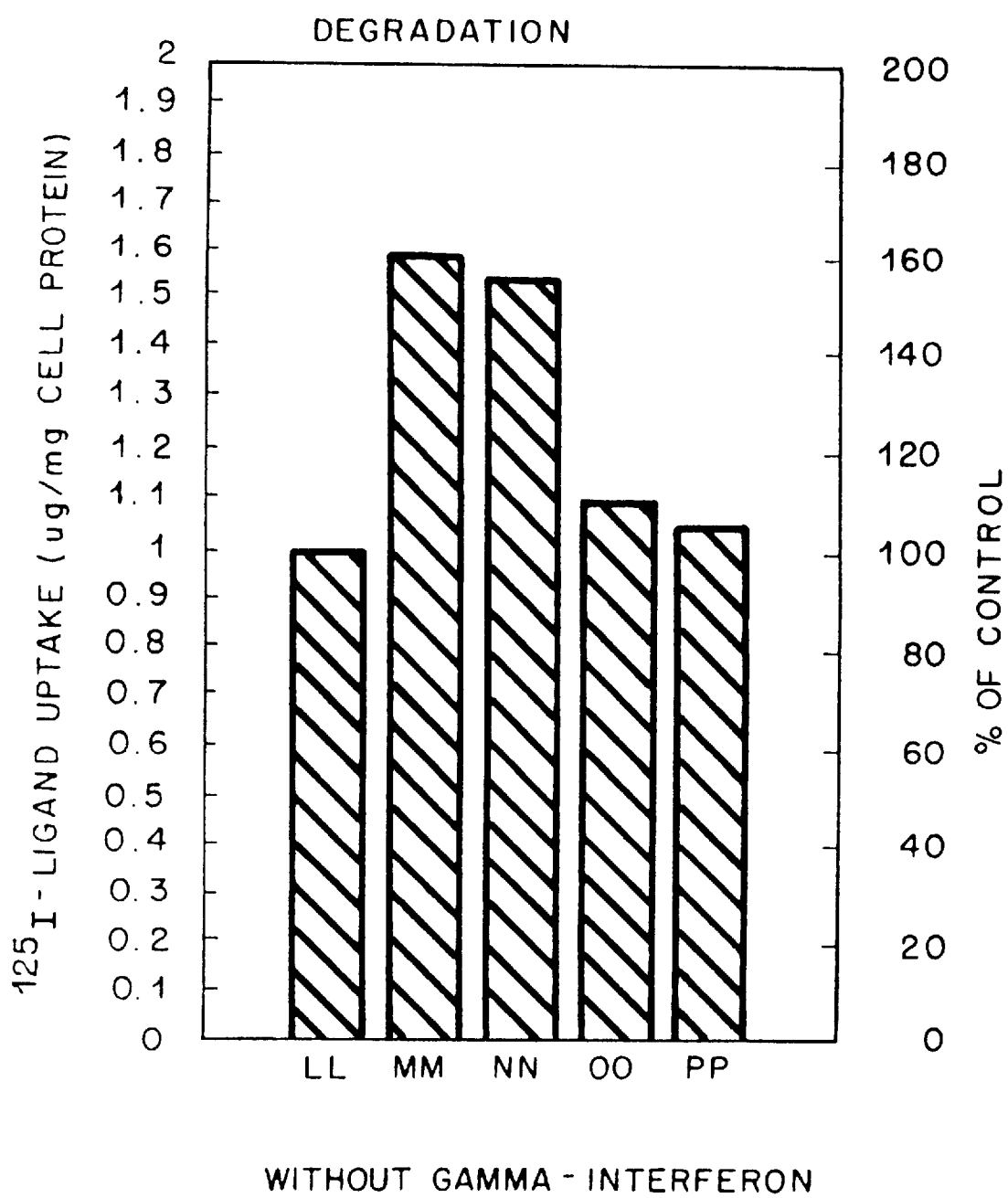
FIG. 5B is a bar graph illustrating the comparative degradation of advanced glycosylation endproducts by mouse macrophages exposed to the following stimulator compounds: LL, control; MM, cachectin (20 mg)+Glu-BSA; NN, cachectin (20 mg)+G6P-BSA; OO, IL-1+G6P-BSA; and PP, LPS+G6P-BSA. Experiments MM, NN, OO and PP each included 25 µg of the respective AGE reagent.

Mouse peritoneal macrophages show increased uptake of AGE-BSA when stimulated with AGE-BSA prepared from glucose-6-phosphate (FIG. 5A, bar GG). Degradation is also increased (FIG. 5B, bar NN).

As discussed earlier, phagocytic cells such as macrophages may be stimulated to become activated and remove AGE-macromolecules after treating the macrophages with a monokine such as with cachectin (synonym=tumor necrosis factor). The structure and properties of cachectin have been previously elucidated by one of the inventors herein. It has been determined that cachectin at a concentration of 20 ng per milliliter of culture fluid stimulates macrophages to express the AGE-receptor and to increase binding, uptake and degradation of AGE-macromolecules. Preincubation of mouse macrophages for 24 hours with 20 ng/ml of cachectin/TNF (without gamma-interferon) followed by incubation with AGE-BSA results in a 4-fold increase in AGE-BSA (made from glucose reacted with albumin) uptake (FIG. 5A, bar FF). Degradation is also increased by 50% of the control (bar MM).

Similarly, preincubation of 1-day old human monocytes for 24 to 48 hours with cachectin without gamma-interferon leads to almost doubling of uptake and degradation of AGE-BSA (FIG. 6A, bar D). Degradation is also increased (bar 1).

The above examples of agents which stimulate macrophages to increase the ability to internalize and degrade AGEs should not be restrictive. Other agents include additional synthetic specific AGEs linked to carrier molecules, other AGEs made from the reaction of sugars with macromolecules, and other monokines which stimulate macrophages to increase their activity toward AGEs.

The method also includes the coadministration of these agents and one or more co-stimulatory agent such as Interleukin-1 and gamma interferon to achieve an even greater stimulation of the body's AGE removal system.

In a further embodiment of the present invention, macrophages could be treated ex vivo with these agents and returned to the body. For example, an extracorporeal blood treatment may be performed in which indwelling lines are placed in a patient's arterial and venous system, and blood is taken from the body, passed through a device and then returned to the patient. The device is contemplated to contain agents which by contact with or exposure to monocytes/macrophages will stimulate them to increase the activity of the AGE removal system. Further, the agents may either be immobilized or may be capable of entering the blood flow. Such an extracorporeal process may be performed alone or jointly with the administration to the patient of other agents to enhance the process, such as the gamma-interferon described above.

Figure 8:
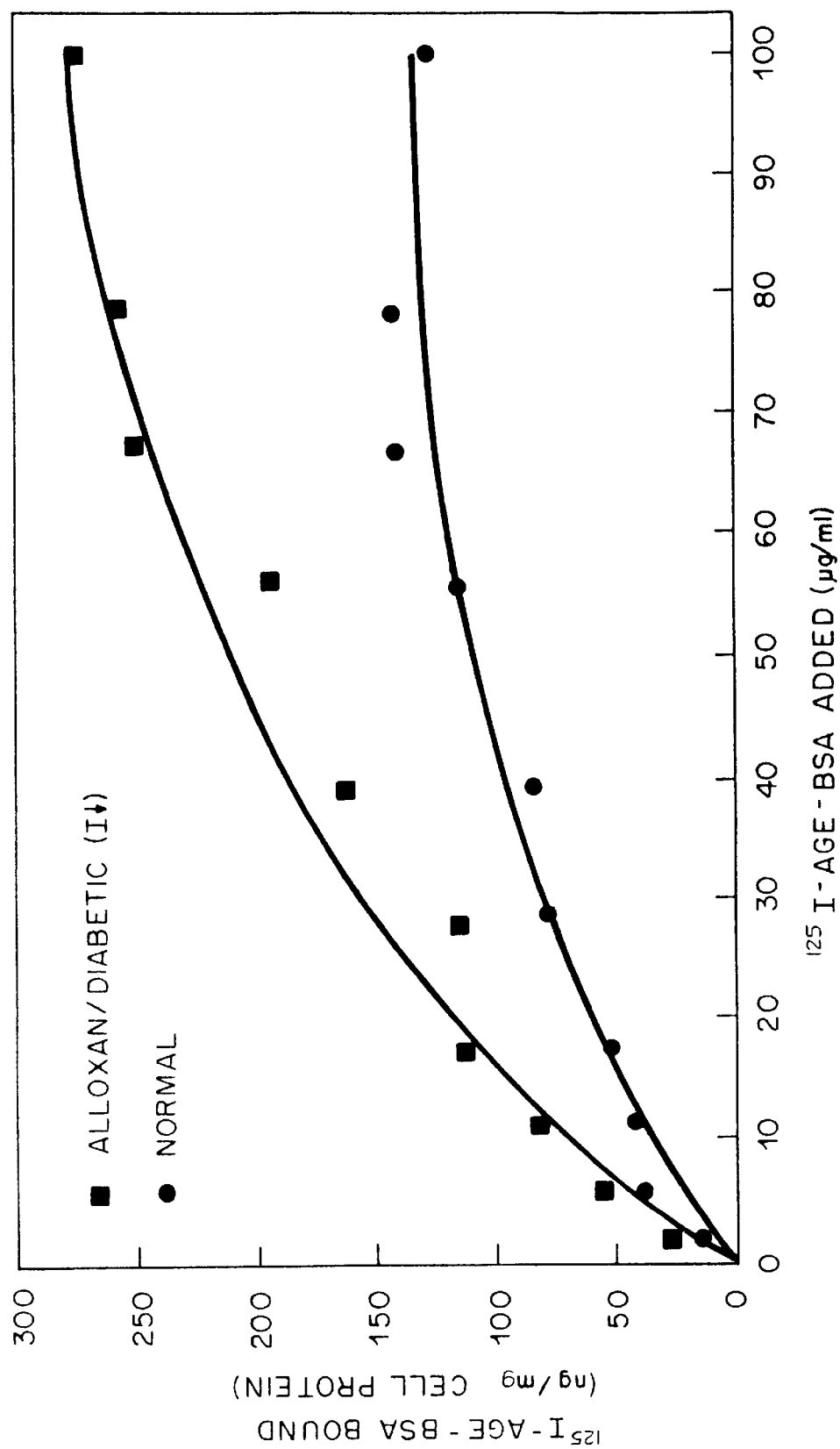
FIG. 8 is a graph illustrating the effect of insulin on the binding capabilities of mouse macrophage cells, wherein a normal sample and an alloxan induced diabetic macrophage sample were compared.
Figure 9:
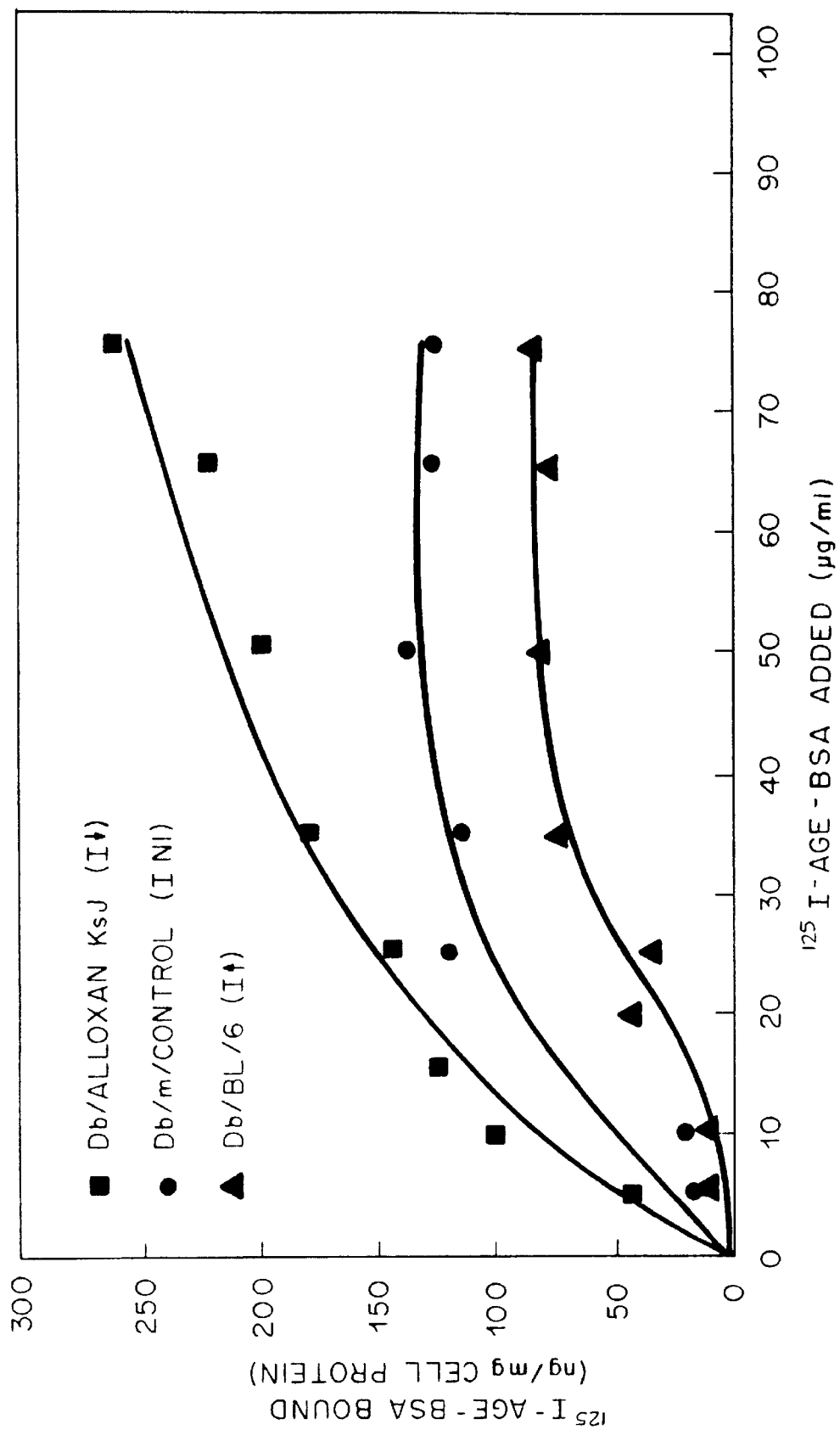
FIG. 9 is a graph similar to FIG. 8, illustrating a comparison between a normal or control sample of human macrophages with those of hypo- and hyper-insulinaemic diabetic macrophages as to the binding capability of each of the samples.

An additional aspect of the present invention herein relates to the observation of the effects of insulin on the macrophage AGE clearance system. It has been found that animals with lower than normal levels of insulin in the blood have an enhanced macrophage AGE clearance system. This has been demonstrated in both experimental animals in which insulin-producing pancreas cells are destroyed by injection of the animal with alloxan, or in genetically diabetic animals which have low insulin levels. In both groups, blood glucose levels are higher than normal. As shown in FIG. 8, animals with experimentally-induced diabetes (using alloxan) and resultant low serum insulin levels (25±6 $\mu$U/ml) had a two-fold greater activity of binding of AGE-BSA to macrophages as compared with normal animals (serum insulin of 74±28 $\mu$U/ml). In FIG. 9, it is apparent that C57BL/KsJ, db/db mice, with genetically low insulin levels (8.2±2 $\mu$U/ml) have a greater degree of AGE-BSA binding to macrophages than control mice.

Figure 10:
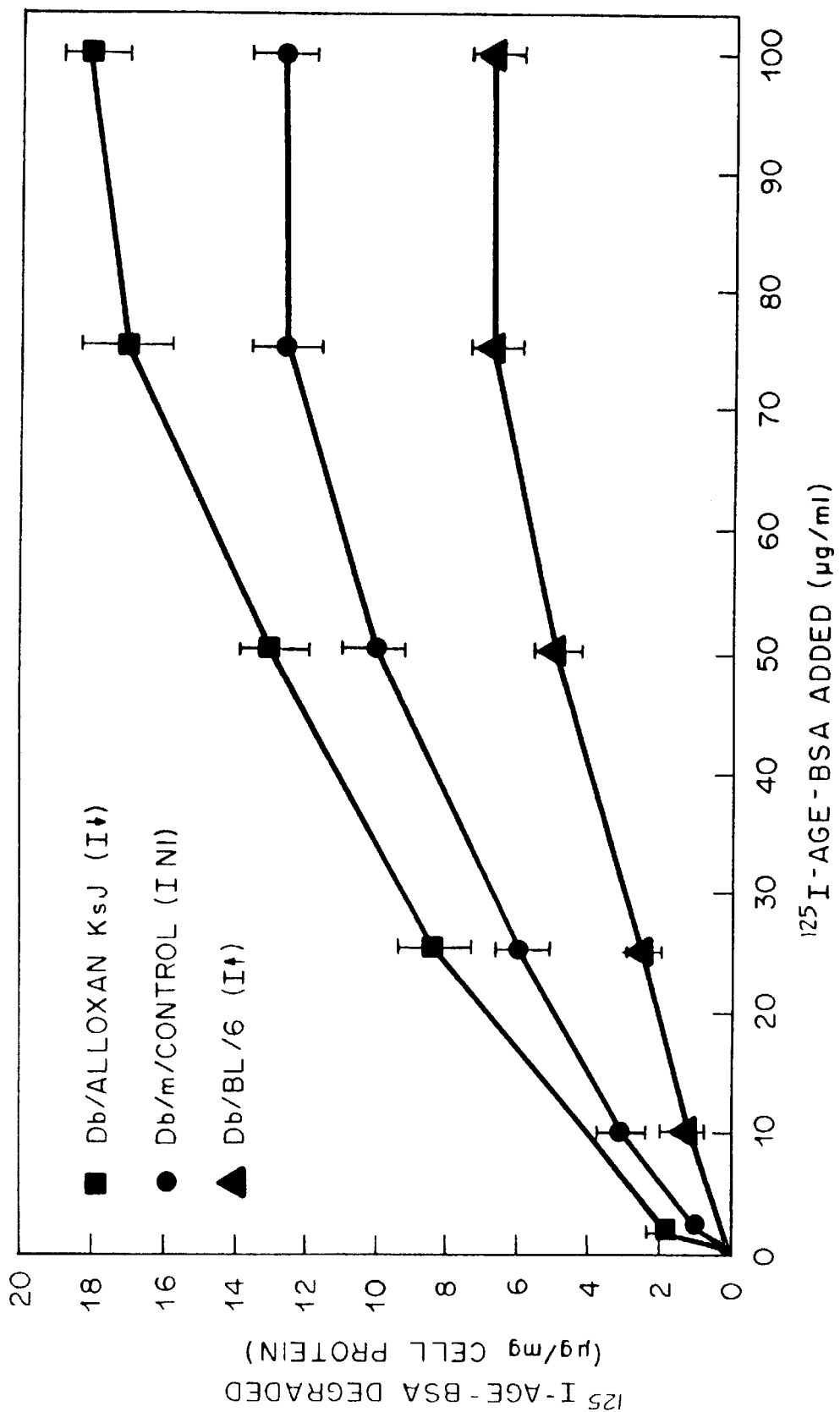
FIG. 10 is a graph similar to FIG. 9, making a comparison between the same macrophage samples as to their ability to degrade advanced glycosylation endproducts.

In contrast, animals with high levels of insulin in the blood, such as genetic hyperinsulinaemic animals (C57BL6, db/db, serum insulin>300 $\mu$U/ml, FIG. 9), have a reduction of about 50% of the activity of binding of AGE-BSA to macrophages compared to normal animals. This suppression of the removal system would have a negative effect since clearance of AGE-macromolecules would be decreased. Degradation of AGE (FIG. 10) shows the same relationship to insulin levels.

It is important to note that both the hypoinsulinaemic and hyperinsulinaemic animals had equally abnormal elevations of glucose in the blood.

The effect of insulin on other macrophage receptors is known, however, this is the first report of the role of insulin in regulating the AGE receptor. Because insulin regulates the glucose level in the blood, and glucose is responsible for the production of AGEs which are removed by macrophages, this novel finding suggests an actual correlation between these three phenomena.

An additional observation derived from the present invention, and one which proposes a possible mechanism for the effects of the present method is that macrophages, on stimulation with FFI-carrier proteins or AGE-proteins, will secrete cachectin into the surrounding fluid. Macrophages are known to produce cachectin in response to certain stimuli, but this is the first report of the monokine being produced in response to FFI and AGE-proteins. Since these moieties exist in the body, production of cachectin may occur during recognition, internalization, or degradation of AGEs. Since cachectin is known to increase the removal system, this observation suggests that cachectin may be involved in an amplification phenomenon to signal other macrophages to increase activity of the removal system. The secretion of cachectin by cells exposed to AGEs may also bring about other effects on cells.

Accordingly, one of the therapeutic methods of the present invention comprises providing cachectin or a derivative of cachectin in amounts sufficient to stimulate the removal system. The exact quantities of cachectin to be administered may vary, and the amounts employed in the experiments with cachectin set forth herein are representative. Naturally, specific amounts would be determined by the attending physical or veterinarian administering the treatment.

A further therapeutic application of the present invention lies in the area of immunology. In particular, the recognition and degradation of advanced glycosylation endproducts, such as FFI by phagocytic cells facilitates the introduction to those cells of certain antigens against which it is desired to raise an immunity. Accordingly, the advanced glycosylation endproduct or FFI could be coupled to an antigen in much the same fashion as disclosed herein for the coupling to any other carrier. Thereafter, the particular phagocytic cells that it is desired to stimulate could be exposed to the coupled complex whereupon the cells would recognize and degrade the latter, and would concomitantly develop specific receptors therefor. These activated phagocytes could then be introduced to the immune system of the animal and would promote the development by the immune system of antibodies to the initial antigen.

The above method may be practiced ex vivo or in vivo. If ex vivo, the method would include the initial removal of the phagocytes from the body and their exposure to the coupled complex to develop their sensitivity to the particular antigen. Thereafter a sample of cells of the animal that is known to be responsible for raising antibodies and that would have been simlarly isolated and removed from the animal, or cells from other sources that may perform the same function, would be exposed to the activated phagocytes for a period of time sufficient to enable antibodies to be raised to the antigen of interest. The antibodies could be administered to animals to avert or alleviate the adverse effects of any pathology that might be caused by the invasion of the antigen.

Alternately the ex vivo activated phagocytes could be utilized as a vaccine to innoculate animals against the antigen and to thereby promote the in vivo development of antibodies thereto.

An in vivo protocol contemplates the preparation of the coupled complex between the AGE/FFI and the antigen and the administration of this coupled complex directly to the animal to promote the in vivo activation of phagocytes and the subsequent development of antibodies by the animal's immune system.

A further alternative contemplates the formation of a mixture rather than a coupled complex between the AGE/FFI and the antigen. This mixture could be utilized in place of the coupled complex in the above protocols.

A particular implementation of the ex vivo embodiment of the immunological protocol could in include the immobilization of either the coupled complex or the phagocytic cells during all or part of the practice of the particular method. Thus, for example, either the cells or the coupled complex could be immobilized and the unbound material then circulated therepast to achieve activation. If it is desired to administer the bound material to the animal, it could be released from the substrate after activation by known techniques.

A further therapeutic protocol is suggested by the foregoing immunological protocols, which is based upon the binding, labeling or other combination of the AGE/FFI in this instance to a particular antigen as defined herein. Thus, the AGE/FFI could be combined with an antibody specific to the particular antigen, and the resulting associated mixture or combined material then placed in contact with the phagocytic cells of the animal/human host to stimulate such cells to recognize and attack the antigen. In such instance, the manner by which contact between the combined material and the phagocytes occurs may vary.

Thereafter, a quantity of the combined material may be introduced in vivo to bind with the target antigen. The stimulated phagocytes would then be introduced or stimulation of the phagocytes would take place concurrently upon the in vivo introduction of the combined material, whereupon the phagocytes would attack and destroy/degrade the complex formed by the combined material and the target antigen, either directly or by means of the secretion of the monokine cachectin/TNF. Regardless of the exact mechanism of final action, the phagocytes would act specifically against the target antigen because of their recognition of the particular AGE/FFI now associated therewith by means of the antibody.

The foregoing therapeutic method may vary as to dosage, manner of administration and periodicity, depending upon the particular host and the attending pathological condition, and is subject to adjustment by the trained physician or veterinarian. This therapy offers a potentially effective avenue of treatment for patients suffering from Acquired Immune Deficiency Syndrome (AIDS) in view of the inability of conventional therapies to alleviate the condition.

All of the above immunological and therapeutic protocols could include the coadministration of one or more of the co-stimulatory agents in the manner set forth earlier herein to potentiate where possible the efficacy of such protocols. The present invention accordingly extends to such variations in its practice.

As mentioned earlier, the present invention contemplates numerous diagnostic applications. In a first application, an assay system may be developed for screening potential drugs effective to act as agents to stimulate the activity of specific phagocytes against advanced glycosylation endproducts. Accordingly, a prospective test drug could be administered to a macrophage sample to determine its stimulatory effect and the macrophage sample after incubation with the test drug could be incubated with a fluid or tissue sample having a quantity of appropriately labeled advanced glycosylation endproducts present therin, so that comparative uptake and degradation studies could then be made. In this assay, plural macrophage colonies could be initially incubated with various of the known agents, so that comparative testing of the prospective drug could take place with greater specificity.

An alternate diagnostic protocol contemplates the investigation of particular phagocytes to determine which of the known agents are most effective in stimulating cellular activity against advanced glycosylation endproducts. Thus, in similar fashion to the protocol described above, plural comparable quantities of a particular phagocytic cell colony could be isolated and incubated with several different known agents, and thereafter incubated with identical corresponding samples containing appropriately labeled advanced glycosylation endproducts, so that a comparason of the extent of activation of the phagocytic cells could then be made, and the agent most effective in stimulating the cellular colony thereby identified. In such manner, the colony exhibiting the greatest uptake and disposal of labeled advanced glycosylation endproducts would correspondingly identify the agent that is most effective.

A further diagnostic utility is predicated upon the study of the various parameters that attend the recognition and removal of advanced glycosylation endproducts and their significance in relation to the operation of animal body systems. In a first embodiment, phagocytic cells such as monocytes and macrophages are removed from the animal's body and are activated ex vivo by exposure to the agents of the present invention. This may be accomplished by an extracorporeal shunt as has been described earlier on herein. After such activation, the phagocytic cells, instead of being returned immediately to the body, are appropriately radiolabeled, as with Technicium, and are then returned to the body, whereupon the animal may undergo radioimaging to note the course of travel of the phagocytes and to thereby determine the location of the concentrations of advanced glycosylation endproducts in the body. In this manner, undesireable concentrations of advanced glycosylation endproducts, such as atheromatous plaques could be discovered, and the clinical significance of these concentrations accordingly assessed. This procedure would provide additional vital information in attempting to assess the pathological state of the animal or patient.

A further diagnostic application likewise seeking to provide vital information regarding pathological status contemplates the preparation of radiolabeled agents and their incubation or contact with phagocytes from a particular animal, and the subsequent measurement of the elapsed time before the labeled agents are recognized and degraded. Such time measurements could be compared against standard measurements determined by testing cells taken from normal animals or patients that were tested under the same protocol. This data could then identify the existence of pathologies such as diabetes, or the others mentioned earlier herein, or other disorders that may adversely affect the operability of the AGE removal system of the body. This diagnostic procedure can be performed in vivo by administering the labeled agents to the animal or patient, or alternatively, could be conducted ex vivo by the isolation of phagocytic cells of the animal or patient outside the body and the incubation of these cells with the labeled agents.

An additional diagnostic technique contemplates a further qualitative analysis of the animal's body. In this procedure particular pathologies may be identified by a method wherein the activity of the phagocytic cells of the animal could be measured and compared against the activities found with normal cells. In such instance, for example, radiolabeled agents could be introduced to the body, or phagocytic cellular colonies from the body could be isolated and incubated with the radiolabeled agents, and the level of activity of the phagocytic cells could then be measured with greater specificity as to particular advanced glycosylation endproducts. This is possible because of the specific nature of the cellular receptors that develop on the phagocytic cells as to particular advanced glycosylation endproducts. Thus, the macrophage or monocytes having greatest involvement with the removal of advanced glycosylation endproducts that would otherwise develop atheromatous plaques, could be isolated and tested for their activity, and if their activity appears to be abnormally increased, the development of such plaques may be indicated. Similar testing protocols could be employed to determine the existence of diabetic aging and the like.

Thus, the specific advanced glycosylation endproducts associated with particular conditions would elicit responses from the phagocytes that would suggest any abnormal accumulation of these advanced glycosylation endproducts in the body system. The presence of particular AGEs in the body reflect correspondingly particular pathologies, and the foregoing observation of the phagocytes and the determination of their sensitivity and increased stimulation with respect to particular advanced glycosylation endproducts would suggest the existence of a particular pathology.

This invention may be embodied in other forms or carried out in other ways without departing from the spririt or essential characteristics thereof. The present disclosure is therefore to be considered as in all respects illustrative and not restrictive, the scope of the invention being indicated by the appended Claims, and all changes which come within the meaning and range of the equivalency are intended to be embraced therein.

What is claimed is:

1. A method for identifying and measuring the extent of a pathological condition due to an accumulation of advanced glycosylation endproducts in an animal, comprising:

isolating from said animal a quantity of phagocytic cells;

attaching to said cells a radioactive label; and introducing said labeled cells into said animal's body and tracing the course of travel and activity of said labeled cells by a radiometric method to determine the location and extent of accumulation of advanced glycosylation endproducts, and to thereby determine the corresponding location and extent of pathologies having such accumulations as a manifestation thereof.

2. The method of claim 1, wherein prior to said introducing step said phagocytic cells are incubated with an agent capable of causing said phagocytic cells to increase their activity of recognizing and removing macromolecules that have undergone advanced glycosylation, said agent selected from the group consisting of an advanced glycosylation endproduct, an advanced glycosylation endproduct bound to a carrier, a monokine that stimulates the phagocytic cells in said body to increase said recognizing and removing activity toward said macromolecules, and mixtures thereof.

3. A method according to claim 1 wherein the agent is selected from the group consisting of the reaction product of albumin and glucose, the reaction product of albumin and glucose-6-phosphate, the fluorescent chromophore 2-(2-furoyl)-4(5)-(2-furanyl)-1H-imidazole bound to a carrier, and mixtures thereof.

4. A method according to claim 3 wherein the carrier is selected from the group consisting of carbohydrates, proteins, lipids, synthetic polypeptides, biocompatible natural and synthetic resins, antigens, and mixtures thereof.

5. A method for measuring the pathological status of an animal patient, said pathological status indicative of the presence or development of pathology resultant from an accumulation of advanced glycosylation endproducts in the body of said animal patient, said accumulation resultant from reduced recognition and removal of advanced glycosylation endproducts by phagocytic cells of said animal patient as compared with that of healthy animals, said method comprising the sequential steps of:

(i) preparing an agent capable of being recognized and removed by phagocytic cells of said animal patient through the recognition and removal of macromolecules that have undergone non-enzymatic advanced glycosylation, said agent selected from the group consisting of an advanced glycosylation endproduct, an advanced glycosylation endproduct bound to a carrier, and mixtures thereof;

(ii) attaching an appropriate label to said agent;

(iii) administering said labeled agent to said animal patient;

(iv) measuring the time required by the body of said animal patient to recognize and remove said labeled agent;

(v) comparing the difference in said time required by the body of said animal patient to recognize and remove said labeled agent with time required by the body of healthy animals to recognize and remove said labeled agent; and (vi) correlating any increased time for recognition and removal of said agent by the body of said animal patient with a decrease in advanced glycosylation endproduct recognition and removal in said animal patient, wherein the extent of said decrease provides said measure of said pathological status.

6. A method according to claim 5 wherein the agent is selected from the group consisting of the reaction product of albumin and glucose, the reaction product of albumin and glucose-6-phosphate, the fluorescent chromophore 2-(2-furoyl)-4(5)-(2-furanyl)-1H-imidazole bound to a carrier, and mixtures thereof.

7. A method according to claim 6 wherein the carrier is selected from the group consisting of carbohydrates, proteins, lipids, synthetic polypeptides, biocompatible natural and synthetic resins, antigens, and mixtures thereof.

8. The method of claim 5 wherein said selected advanced glycosylation endproduct or advanced glycosylation endproduct bound to a carrier is specifically associated with a particular pathology, and said measure of pathological status is specific to said pathology.

9. A method for measuring the pathological status of an animal patient, said pathological status indicative of the presence or development of pathology resultant from an accumulation of advanced glycosylation endproducts in the body of said animal patient, said accumulation resultant from reduced recognition and removal of advanced glycosylation endproducts by phagocytic cells of said animal patient as compared with that of healthy animals, said method comprising the sequential steps of:

(i) preparing an agent capable of being recognized and removed by phagocytic cells of said animal patient through the recognition and removal of macromolecules that have undergone non-enzymatic advanced glycosylation, said agent selected from the group consisting of an advanced glycosylation endproduct, an advanced glycosylation endproduct bound to a carrier, and mixtures thereof;

(ii) attaching an appropriate label to said agent;

(iii) isolating a sample of phagocytic cells from said animal patient and incubating said cells with said labeled agent;

(iv) measuring the time required by said sample to recognize and remove said labeled agent;

(v) comparing the difference in said time required by said cellular sample to recognize and remove said labeled agent with time required by cellular samples of healthy animals to recognize and remove said labeled agent; and (vi) correlating any increased time for recognition and removal of said agent by said cellular sample from said animal patient with a decrease in advanced glycosylation endproduct recognition and removal of said cellular sample of said animal patient, wherein the extent of said decrease provides said measure of said pathological status.

10. A method according to claim 9 wherein the agent is selected from the group consisting of the reaction product of albumin and glucose, the reaction product of albumin and glucose-6-phosphate, the fluorescent chromophore 2-(2-furoyl)-4(5)-(2-furanyl)-1H-imidazole bound to a carrier, and mixtures thereof.

11. A method according to claim 10 wherein the carrier is selected from the group consisting of carbohydrates, proteins, lipids, synthetic polypeptides, biocompatible natural and synthetic resins, antigens, and mixtures thereof.

12. A method according to claim 9 wherein the extent of the activation of the cells of the sample is additionally measured to determine the amount and identity of the advanced glycosylation endproducts present.

13. The method of claim 9 wherein said selected advanced glycosylation endproduct or advanced glycosylation endproduct bound to a carrier is specifically associated with a particular pathology, and said measure of pathological status is specific to said pathology.

* * * * *